(12) United States Patent
Messadek

(10) Patent No.: US 7,786,077 B2
(45) Date of Patent: Aug. 31, 2010

(54) INSULINS COMBINATIONS

(76) Inventor: Jallal Messadek, Place des Beguinages 2, B-4000, Liege (BE)

( * ) Notice: Subject to any disclaimer, the term of this patent is extended or adjusted under 35 U.S.C. 154(b) by 0 days.

(21) Appl. No.: 11/927,172

(22) Filed: Oct. 29, 2007

(65) Prior Publication Data

US 2008/0214441 A1    Sep. 4, 2008

Related U.S. Application Data

(63) Continuation-in-part of application No. PCT/BE2006/000040, filed on Apr. 27, 2006, and a continuation-in-part of application No. PCT/BE2005/000061, filed on Apr. 27, 2005, now abandoned.

(51) Int. Cl.
- A61K 38/28 (2006.01)
- A61P 3/10 (2006.01)
- A01N 57/26 (2006.01)
- C07K 4/00 (2006.01)

(52) U.S. Cl. .................. 514/4; 514/3; 514/77; 530/303
(58) Field of Classification Search ........................ None
See application file for complete search history.

(56) References Cited

U.S. PATENT DOCUMENTS

| | | |
|---|---|---|
| 3,577,534 A | 5/1971 | Koh et al. |
| 4,066,756 A | 1/1978 | Orr et al. |
| 4,605,548 A | 8/1986 | Ushiyama et al. |
| 4,703,045 A | 10/1987 | Guinot |
| 4,814,179 A | 3/1989 | Bolton et al. |
| 4,902,718 A | 2/1990 | Bayless et al. |
| 4,911,916 A | 3/1990 | Cleary |
| 4,968,719 A | 11/1990 | Brevetti |
| 5,342,621 A | 8/1994 | Eury |
| 5,405,614 A | 4/1995 | D'Angelo et al. |
| 5,716,941 A | 2/1998 | Rabinoff |
| 5,814,599 A | 9/1998 | Mitragotri et al. |
| 5,876,780 A | 3/1999 | Vertanen |
| 5,880,098 A | 3/1999 | Haussinger |
| 5,928,195 A | 7/1999 | Malamud et al. |
| 5,961,999 A | 10/1999 | Bimczok et al. |
| 6,008,221 A | 12/1999 | Smith et al. |
| 6,235,311 B1 | 5/2001 | Ullah et al. |
| 6,287,765 B1 | 9/2001 | Cubicciotti |
| 6,355,166 B1 | 3/2002 | Amarasinghe et al. |
| 6,399,785 B1 | 6/2002 | Murphy et al. |
| 6,476,006 B2 | 11/2002 | Flashner-Barak et al. |
| 6,504,005 B1 * | 1/2003 | Fridkin et al. ............... 530/303 |
| 6,624,180 B2 | 9/2003 | South et al. |
| 6,762,025 B2 | 7/2004 | Cubicciotti |
| 6,855,734 B2 | 2/2005 | Messadek |
| 6,881,420 B2 | 4/2005 | Flashner-Barak et al. |
| 7,097,968 B2 | 8/2006 | Yuan et al. |
| 2002/0034757 A1 | 3/2002 | Cubicciotti |
| 2002/0065320 A1 | 5/2002 | Messadek |
| 2002/0183380 A1 | 12/2002 | Hunter |
| 2003/0054978 A1 | 3/2003 | Babish |
| 2003/0124705 A1 | 7/2003 | Berry et al. |
| 2003/0203385 A1 | 10/2003 | Venkataraman et al. |
| 2003/0203878 A1 | 10/2003 | Flashner-Barak et al. |
| 2004/0033223 A1 | 2/2004 | Messadek |
| 2004/0043442 A1 | 3/2004 | Jutila et al. |
| 2004/0067986 A1 | 4/2004 | Sassover |
| 2004/0072750 A1 | 4/2004 | Phillips et al. |
| 2005/0013866 A1 | 1/2005 | Maincent et al. |
| 2006/0034918 A1 | 2/2006 | Messadek |
| 2006/0128657 A1 | 6/2006 | Messadek |
| 2006/0160896 A1 | 7/2006 | Messadek |
| 2006/0233877 A1 | 10/2006 | Messadek et al. |
| 2007/0134324 A1 | 6/2007 | Messadek |
| 2007/0213399 A1 | 9/2007 | Messadek |
| 2008/0031964 A1 | 2/2008 | Messadek |

FOREIGN PATENT DOCUMENTS

| | | |
|---|---|---|
| BE | 1012546 | 12/2000 |
| BE | 1012712 | 2/2001 |
| BE | 2003/0248 | 4/2003 |
| DE | 19910682 | 9/2000 |
| EP | 0347864 | 12/1989 |
| EP | 0349902 | 1/1990 |
| EP | 0781554 | 7/1996 |

(Continued)

OTHER PUBLICATIONS

Carman and Fernandez, "A Primary Care Approach to the Patient with Claudication," American Family Physician, vol. 61, No. 4, Feb. 15, 2000, http://www.aafp.org/afp/20000215/1027.html, 8 pages.

(Continued)

*Primary Examiner*—Robert Landsman
*Assistant Examiner*—Ian Dang
(74) *Attorney, Agent, or Firm*—Hovey Williams LLP

(57) ABSTRACT

A pharmaceutical association or combination comprising a therapeutic effective amount of insulin or insulin analogue, and a therapeutic effective amount of a pharmaceutically acceptable betaine, in which the insulin and the betaine possibly form a chemical entity or complex, and in which the amount of betaine is adapted for controlling the degradation and/or for increasing the duration of action and/or for enhancing the therapeutically effect of the insulin or insulin analogue.

20 Claims, 6 Drawing Sheets

FOREIGN PATENT DOCUMENTS

| | | |
|---|---|---|
| FR | 2590 M | 3/1963 |
| FR | 70.47549 | 12/1970 |
| FR | 77 29075 | 9/1977 |
| HU | 210122 B | 9/1992 |
| JP | 2000-143486 | 5/2000 |
| JP | 10321984 | 5/2000 |
| WO | 9515750 | 6/1995 |
| WO | 9706795 | 2/1997 |
| WO | 9738685 | 10/1997 |
| WO | WO 97/38686 | 10/1997 |
| WO | 9819690 | 5/1998 |
| WO | WO 98/56497 | 12/1998 |
| WO | WO 99/45913 | 9/1999 |
| WO | 0025764 | 5/2000 |
| WO | 0051596 | 9/2000 |
| WO | WO 01/56609 | 8/2001 |
| WO | WO 02/00213 | 1/2002 |
| WO | WO 02/47493 | 6/2002 |
| WO | WO 02/062322 | 8/2002 |
| WO | WO 02/066002 | 8/2002 |
| WO | WO 2004/032916 | 4/2004 |
| WO | WO 2004/049095 | 6/2004 |
| WO | WO 2004/091601 | 10/2004 |
| WO | WO 2005/004854 | 1/2005 |
| WO | WO 2005/011642 | 2/2005 |
| WO | WO 2005/011645 | 2/2005 |
| WO | WO 2005/065675 | 7/2005 |
| WO | WO 2006/007671 | 1/2006 |
| WO | WO 2006/050581 | 5/2006 |
| WO | WO 2006/050585 | 5/2006 |

OTHER PUBLICATIONS

Beaufour and Beaufour, "Nouvelles associations antinévralgiques à tolérance ameéliorée," Brevet Spécial De Médicament. P.V. No. 927.734, No. 2.590, 1964, pp. 1-5.

Feb. 23, 1996 Chinese document (pp. 91-93) with English translation titled "Homocysteine and Vascular Disease," 5 pages.

Da Silva and Sobel, Abstract from Entrez-PubMed web page entitled "Anicoagulants: to bleed or not to bleed, that is the question," Semin Vasc. Surg. Dec. 2002;;15(4):256-67, 1 page.

JACC Abstracts, Myocardial Ischemia and Infarction, Feb. 2000, 1196-107, pp. 408-409.

Lasch H.G., Abstract from Entrez-PubMed web page entitled "Principles of Drug Prevention of Thrombosis," Langenbecks Arch Chir., 1986;369:451-7, 1 page.

Marcel et al., Abstract from Entrez-PubMed web page entitled "From Virchow to red cells (the unended quest).", Ric Clin Lab., 1983;13 Suppl 3:71-81, 1 page.

I. Zöllei et al., Betaine-Palmitate Reduces Acetylsalicyclic Acid-induced Gastric Damage in Rats, Scand J. Gastroenterol 2001 (8), pp. 811-816.

Antithrombotic effect of Betaine, Bio Ethic, Jan. 2003, pp. 1-30.

Office Action in U.S. Appl. No. 09/945,391 dated Nov. 5, 2002, 5 pages.

Office Action in U.S. Appl. No. 09/945,391 dated Jun. 4, 2003, 14 pages.

Office Action in U.S. Appl. No. 10/635,048 dated Dec. 6, 2005, 8 pages.

Office Action in U.S. Appl. No. 10/635,048 dated Dec. 21, 2006, 16 pages.

Office Action in U.S. Appl. No. 10/635,048 dated Sep. 20, 2007, 25 pages.

Bidulescu et al., Usual choline and betaine dietary intake and incident coronary heart disease: the Atherosclerosis Risk in Communities (ARIC) Study,BMC Cardiovesc Disord. 2007, 7:20.

Hallas et al., "Use of single and combined antithrombotic therapy and risk of serious upper gastrointestinal bleeding: population based case-control study," BMJ 2006;333:726, Oct. 7, 2006.

Casser, "Intermittent Claudication," BMJ, vol. 333, Nov. 11, 2006, pp. 1002-1005.

Apgar, "Efficacy of Cilostazol for Intermittent Claudication," American Family Physician, Feb. 15, 2000, 2 pages.

Girolami et al., "Treatment of Intermittent Claudication with Physical Training, Smoking Cessation, Pentoxifylline, or Nafronly," Arch Intern med, 1999;159:337-345.

Office Action in U.S. Appl. No. 11/747,167 dated May 12, 2008, 5 pages.

Giaid et al, "Expression of Endothelin-1 in the Lungs of Patients with Pulmonary Hypertension," NEJM, vol. 328:1732-1739, No. 24, Jun. 17, 1993, 2 pages.

Giaid et al., "Reduced Expression of Endothelial Nitric Oxide Synthase in the Lungs of Patients with Pulmonary Hypertension," NEJM, vol. 333:214-221, No. 4, Jul. 27, 1995, 2 pages.

International Search Report mailed Jan. 22, 2007 for applicant Jallal Messadek's PCT Application No. PCT/BE2006/000040 filed on Apr. 27, 2006.

Written Opinion for applicant Jallal Messadek's PCT Application No. PCT/BE2006/000040 filed on Apr. 27, 2006.

Office Action in U.S. Appl. No. 11/251,737 dated Oct. 29, 2008, 21 pages.

Office Action in U.S. Appl. No. 10/635,048 dated Aug. 6, 2008, 13 pages.

Office Action in U.S. Appl. No. 11/333,514 dated Sep. 8, 2008, 26 pages.

Hiatt, "New Treatment Options in Intermittent Claudication: The US Experience," International Journal of Clinical Practice (2001) 119:20-27.

Office Action in U.S. Appl. No. 11/333,514 dated Mar. 20, 2009, 12 pages.

Office Action in U.S. Appl. No. 11/348,142 dated Jan. 28, 2009, 26 pages.

Office Action in U.S. Appl. No. 11/747,167 dated Aug. 18, 2008, 21 pages.

Office Action in U.S. Appl. No. 11/747,167 dated Feb. 10, 2009, 11 pages.

Zhang et al., "Upregulation of Vascular Arginase in Hypertension Decreases Nitric Oxide-Mediated Dilation of Coronary Arterioles," Hypertension, 2004;44;935-943.

Taddei et al., "Role of Endothelin in the Control of Peripheral Vascular Tone in Human Hypertension," Heart Failure Reviews, 2001, 6, 277-285.

Office Action in U.S. Appl. No. 11/251,737 dated Apr. 17, 2008, 7 pages.

Office Action in U.S. Appl. No. 11/333,514 dated Sep. 20, 2007, 12 pages.

Office Action in U.S. Appl. No. 11/333,514 dated Nov. 15, 2007, 11 pages.

McGregor et al, "A Controlled Trial of the Effect of Folate Supplements on Homocysteine, Lipids and Hemorheology in End-State Renal Disease," Nephron, vol. 85, No. 3, 2000, 215-220.

Gurfinkel et al., "Fast platelet suppression by lysine acetylsalicylate in chronic stable coronary patients. Potential clinical impact over regular aspirin for coronary syndromes," *Clin. Cardiol.*, Sep. 2000;23(9):697-700.

Klasing et al., "Dietary Betaine Increases Intraepithelial Lymphocytes in the Duodenum of Coccidia-Infected Chicks and Increases Functional Properties of Phagocytes," 2002, *The American Society for Nutritional Sciences*, J. Nutr, 132:2274-2282, 2002.

Schmidt et al., "Total nitric oxide production is low in patients with chronic renal disease," Kidney International, 2000, 58, 1261-1266.

Letter Regarding Dietary Supplement Health Claim for Folic Acid, Vitamin B6, and Vitamin 312 and Vascular Disease, to Jonathan W. Emord of Emord & Associates, PC, from Christine J. Lewis of the FDA, Nov. 28, 2000.

Malinow, "Plasma homocyst(e)ine and arterial occlusive diseases: a mini-review," *Clin. Chem*, Jan. 1995;41(1) 73-6.

al Awami et al., "Homocysteine levels in patients with Raynaud's phenomenon," Vasa. May 2002; 31(2): 87-90.

Stammler et al., "The prevalence of hyperhomocysteinemia in thromboangitis obliterans. Does homocysteine play a role pathogenetically?" *Dtsch Med Wochenschr*, Nov. 1996 15;121(46):1417-23.

English Translation of French Patent 2,590M issued on Jun. 15, 1964, 11 pages.

McCarty, "Co-administration of equimolar doses of betaine may alleviate the hepatotoxic risk associated with niacin therapy," Med-Hypothesis, Sep. 2000; 55(3): 189-94.

Letter regarding Petition for Health Claim: Folic Acid, Vitamin B6, and Vitamin B12 Dietary Supplements and Vascular Disease, to Jonathan W. Emord of Emord & Associatees from Christine J. Lewis of the FDA, Feb. 9, 2001.

Birnie et al., "Antimicrobial Evaluation of N-Alkyl Betaines and N-Alkly-N,N-Dimethylamine Oxides with Variations in Chain Length," Antimicrobial Agents and Chemotherapy. Sep. 2000, p. 2514-2517.

Palatka Karoly et al., "Changes in the expression and distribution of the inducible and endothelial nitric oxide synthase in mucosal biopsy specimens of inflammatory bowel disease," Scandinavian Journal of Gastroenerology, 2005, vol. 40, No. 6, pp. 670-680.

van Hoek, "Non-alcoholic fatty liver disease: a brief review," Scandinavian Journal of Gastroenerology Supplement, 2004;(241):56-9.

Mendes et al., "Recent advances in the treatment of non-alcoholic fatty liver disease," Export Opin. Investig. Drugs, Jan. 2005;14(1):29-35.

Hiatt et al, Long-term safety of cilostazol in patients with peripheral artery disease, The CASTLE study (Cilostazol: A Study in Long-term Effects), Journal of Vascular Surgery, vol. 47, No. 2, pp. 330-336, Feb. 2008.

Korzh, "Relationship Between Endothelial Nitric Oxide Synthesis and Low-Grade Chronic Inflammation," European Atherosclerosis Society, 73rd EAS Congress, Salzburg, Austria, Jul. 7-10, 2002.

Didier et al., "Distal cutaneous necrosis, an unusual etiology: hyperhomocysteinemia," Ann Dermatol Venereol, Nov. 1999;126(11):822-5; PMID: 10612875.

Gurfinkel et al., "Fast Platelet Suppression by Lycine Acetylsalicylate in Chronic Stable Coronary Patients. Potential Clinical Impact Over Regular Aspirin for Coronary Syndromes," Abstracts—Myocardiol Ischemia and Infarction. *JACC*, Feb. 2000, 408A-409A.

Bonaa et al., Homocysteine lowering and cardiovascular events after acute myocardial infarction,: *N. Eng. J. Med.*, Apr. 13, 2006; 354(15):1578-88, Epub Mar. 12, 2006.

Lonn et al., "Homocysteine lowering folic acid and B vitamins in vascular disease," *N. Eng. J. Med.*, Apr. 13, 2006;354(15):1567-77. Epub Mar. 12, 2006.

Approval of Cilostazol, Jan. 6, 2006, Center for Drug Evaluation and Research, wvvw.fda.gov/cder/news/cilostazol/approval.htm.

Diagnosis and Management of Peripheral Arterial Disease: A National Clinical Guideline, Scottish Intercollegiate Guidelines Network, Oct. 2006, www.sign.ac.uk.

Hiatt, "Medical Treatment of Peripheral Arterial Disease and Claudication," N Engl J Med, vol. 344, No. 21, May 24, 2001, pp. 1608-1621.

Hiatt "The US experience with cilostazol in treating intermitten claudication," Atherosclerosis Supplements 6 (2006) 21-31.

Savi et al., Abstract from Entrez-PubMed web page entitled "SR 121787, a new orally active fibrinogen receptor antagonist," Thromb Haemost, Sep. 1998:80(3):469-76., 1 page.

Banno et al., Abstract from Entrez-PubMed web page entitled "Antiaggregatory, antithrombotic effects of MS-180, a novel platelet glycoprotein IIb/IIIa receptor antagonist," Eur J Pharmacol., Feb. 19, 1999;367(2-3):275-82., 1 page.

Ramjit et al., Abstract from Entrez-PubMed web page entitled "Antithrombotic effects of MK-0852, a platelet fibrinogent receptor antagonist, in canine models of thrombosis," J Pharmacol Exp Ther., Sep. 1993;266(3):1501-11, 2 pages.

Hoffmann et al., Abstract from Entrez-PubMed web page entitled "Prevention of thrombosis and enhancement of thrombolysis in rabbits by SR 121787, a glycoprotein II/III antagnoist," J Pharmacol Exp Ther., Aug. 1998;286(2):670-5., 1 page.

Packham, Abstract from Entrez-PubMed web page entitled "Role of platelets in thrombosis and hemostasis." Can J Physiol Pharmacol., Mar. 1994;72(3):278-84., 1 page.

Lynch et al., Abstract from Entrez-PubMed web page entitled "Nonpeptide glycoprotein IIb/IIIa inhibitors. 5. Antithrombotic effects of MK-0383," J Pharmacol Exp Ther., Jan. 1995;272(1):20-32., 2 pages.

Katada et al, Abstract from Entrez-PubMed web page entitled "The in vitro and in vivo pharmacological profiles of a platelet glycoprotein IIb/IIIa antagonist, NSL-9403," Thromb Res., Oct. 1, 1997;88(1):27-70., 1 page.

Ogawa et al., Abstract from Entrez-PubMed web page entitled "Antiplatelet and antithrombotic effects of orbofiban, a new orally active GPIIb/IIIa antagonist, in guinea pigs," Thromb Res., Mar. 1, 2000;97(5):307-15, 1 page.

Zapadniuk, Abstract from Entrez-PubMed web page entitled "Cholagogic effect of trimethylglycine in normal animals of different ages and in experimental atherosclerosis," Biull Eksp Biol Med., Jul. 1987;104(7):30-2., 2 pages.

Panteleimonova, Abstract from Entrez-PubMed web page entitled "Effect of trimethylglicine on lipid metabolism in experimental atherosclerosis in rabbits," Farmakol Toksikol, Jul.-Aug. 1983;46(4):83-5., 1 page.

Fazio et al., "Treatment of Human Atherosclerosis with Betaine," Minerva Med, Apr. 25 1961, pp. 1511-1516, XP-000853747.

P.H. List et al., "Hagers Handbuch Der Pharmazeutischen Praxis," 1972, Pringer Verlag, Berlin Heidelberg, New York, p. 431, XP-002123167.

Wilcken et al., "The natural history of vascular disease in homocystinuria and the effects of treatment," J. Inher. Metab. Dis. 20(1997) 295-230.

Betaine for Homocystinuria, The Medical Letter, vol. 39, Issue 993, Jan. 31, 1997, p. 12, XP-000853853.

Reynolds, Betaine Hydrochloride, Matindale, The Extra Pharmacopoeia, 1996, Royal Pharmaceutical Society, London, p. 1679, XP-002123168.

1225. Betaine, The Merck Index, 1996 Merck and Co., Whithouse Stations, NJ, p. 198, XP-002123169.

Mar et al., Abstract from Entrez-PubMed web page entitled "Betaine in wine: answer to the French paradox?" Med Hypotheses, Nov. 1999;53(5):383-5., 2 pages.

Salamone et al, "Changes in blood coagulation in experimental subacute poisoning with p-dichlorobenzene. The influence of some lipotropic factors," Journal, Answer 13 of 13, Copyright 2003, ACS, 1 page.

Vinson et al., "New Drug Approvals of 1996-Part 3," Drug Topics, Mar. 17, 1997, University of Mississippi School of Pharmacy, pp. 72-81.

Matthews et al., An indirect response model of homocysteine suppression by betaine: optimising the dosage regimen of betaine in homocystinuria,: 2002 Blackwell Solent Ltd Br J Clin Pharmacol, 54, 140-146.

Schwahn et al, "Pharmacokinetics of oral betaine in healthy subjects and patients with homocystinuria," 2003 Blackwell Scient Ltd Br J Clin Pharmacol, 55, 6-13.

Bandfield et al., "Naproxen, Naproxen Sodium, and Naproxen Betainate Sodium Monohydrate Salts," Pharmaceutics 1, Apr. 14, 2001, pp. 1-5.

van Hecken et al., Abstract from Entrez-PubMed web page entitled "Effect of clopidogrel on naproxen-induced gastrointestinal blood loss in healthy volunteers," Drug Metabol Drug Interact, 1998;14(3):193-205., 1 page.

EC-Naprosyn, Naprosyn, Anaprox, Naprosyn, Rx Only, Roche Pharmaceuticals, Copyright 1999-2004 by Roche Laboratories Inc., pp. 1-20.

Environmental and Health Assessment of Substances in Household Detergents and Cosmetic Detergent Products, Environment Project, 615, 2001, 6.1 Betaines, http:www2.mst.dk/common/Udgivramme/Frame.asp?pg=http://www2.mst.dk/udgiv/Publications/2001/87-7944-596-9/html/helepubl_eng.htm, 1 page.

Wyrick P.B. et al., The Microbicidal Agent C31G Inhibits Chlamydia Trachomatis Infectivity in vitro., *Antimicrob Agents Chemother*, Jun. 1997, 41(6):1335-44, PMID: 9174195, 1 page.

Thompson, K.A. et al., Assessment of the Anti-Microbial Agent C31G as a Spermicide: Comparison with Nonoxynol-9, *Contraception*, May 1996, 53(5): 313-8, PMID: 8724622, 1 page.

Rogers J.S., Abstract from Entrez-PubMed web page entitled "Hypercoagulable states," W V Med J., Feb. 1993;89(2):61-3, 1 page.

Nielsen H.K., Abstract from Entrez-PubMed web page entitled "Pathophysiology of venous thromboembolism," Semin Thromb Hemost, 1991:17 Suppl 3:250-3, 1 page.

Silver et al., Abstract from Entrez-PubMed web page entitled "The caput medusae of hypercoagulability," J. Vasc. Surg., Feb. 2000:31(2):396-405, 1 page.

Swan M.A., "Improved Preservation of the Ram Spermatozoan Plasma Membrane using Betaine in the Primary Fixative," J. Microsc., Sep. 1997, 187(pt 3): 167-9, PMID: 9351233, 1 page.

Thomas, K.C. et al., Effects of Particulate Materials and Osmoprotectants on Very-High-Gravity Ethanolic Fermentaiont by Saccharomyces Cerevislae, Appl Environ Microbiol, May 1994, 60(5): 1519-24, PMID: 801734, 1 page.

Chambers, S. et al., The Osmoprotective Properties of Urine for Bacteria: The Protective Effect of Betaine and Human Urine Against Low pH and High Concentrations of Electrolytes, Sugars, and Urea, *J. Infect Dis.*, Dec. 1985, 152(6): 1308-16, PMID: 3905988, 1 page.

Smith, L.T., Role of Osmolytes in Adaptation of Osmotically Stressed and Chill-Stressed Listeria Monocytogenes Grown in Liquid Media and on Processed Meat Surfaces, *Appl Environ Microbiol*, Sep. 1996, 62(9): 3086-93, PMID: 8795194, 1 page.

Peddie B.A. et al., Is the Ability of Urinary Tracy Pathogens to Accumulate Glycine Betaine a Factor in the Virulence of Pathogenic Strains?, *J. Lab. Clin. Med.*, Oct. 1996, 128(4): 417-22, PMID: 8833891, 1 page.

Koskinen, E. et al., A Preliminary Study on the Use of Betaine as a Cryoprotective Agent in Deep Freezing of Stallion Semen, *Zentralbl Veterinarmed A.*, Feb. 1989, 36(2): 110-4, PMID: 2501949, 1 page.

Swan M.A., Improved Preservation of Ultrastuctural Morphology in Human Spermatozoa Using Betaine in the Primary Fixative, Int. J. Androl., Feb. 20, 1997(1): 45-54, PMID: 9202990, 1 page.

* cited by examiner

INSULINS COMBINATIONS

RELATED APPLICATIONS

This application is a continuation-in-part application of: PCT/BE2006/000040 filed on Apr. 27, 2006, published under WO2006/113978 and claiming the priority of PCT/BE2005/000061 filed on Apr. 27, 2005, and now abandoned, both of which are incorporated by reference.

FIELD OF INVENTION

The present invention provides pharmaceutical compositions and methods for the treatment of diabetes mellitus using combination therapy. The compositions relate to a compound selected from one or more of betaines, lipidic betaines, betaine lipids and an antidiabetic agent such insulins. The methods include the administration of the combination of compound of Formula I, preferably glycine betaine (n=1), with antidiabetic agent where the two components are delivered in a simultaneous manner, where the compound selected from one or more of betaines, lipidic betaines, betaine lipids is administered first, followed by the antidiabetic agent, as well as wherein the antidiabetic agent is delivered first followed by the compound selected from one or more of betaines, lipidic betaines, betaine lipids. In the claims, betaine means pharmaceutically acceptable betaine, lipidic betaines, betaine lipids, pharmaceutically acceptable salts thereof and combinations thereof. The invention further relates to a pharmaceutical composition comprising insulin and a betaine wherein the betaine is used to enhance the insulin effects and/or durations.

In general, the present invention relates to pharmaceutical compositions, and more particularly, to pharmaceutical compositions for the treatment of diabetes mellitus using combination therapy. Betaines combinations with insulins extend the half life and augment the efficiency of insulins, while protecting patients from cardiovascular events.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is partly or completely lost. About 5% of all people suffer from diabetes. Since the introduction of insulin in the 1920's, continuous strides have been made to improve the treatment of diabetes mellitus. To help avoid extreme glycemia levels, diabetic patients often practice multiple daily injection therapy, whereby, for example, fast-acting insulin is administered with each meal and long-acting or intermediate-acting insulin is administered once or twice daily to cover the basal need.

In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin. As diabetic patients are treated with insulin for several decades, there is a major need for safe and life quality improving insulin formulations. Some of the commercially available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both. In addition, some patients are using formulations having both a fast onset of action and a more prolonged action. Such a formulation may be an insulin solution wherein protamine insulin crystals are suspended. Some patients do themselves prepare the final formulation by mixing a fast acting insulin solution with a protracted acting insulin suspension formulation in the ratio desired by the patient in question.

Human insulin consists of two polypeptide chains, the so-called A and B chains which contain 21 and 30 amino acid residues, respectively. The A and B chains are interconnected by two cystine disulphide bridges. Insulin from most other species has a similar construction, but may not contain the same amino acid residues at the same positions.

The development of the process known as genetic engineering has made it possible to prepare a great variety of insulin compounds being analogous to human insulin. In these insulin analogues, one or more of the amino acids have been substituted with other amino acids which can be coded for by the nucleotide sequences. All these compounds might be suitable to be combined with betaines according to the present invention.

Normally, insulin formulations are administered by subcutaneous injection. What is important for the patient is the action profile of the insulin formulation which is the action of insulin on the glucose metabolism as a function of the time from the injection. In this profile, inter alia, the time for the onset, the maximum value, and the total duration of action are important. A variety of insulin formulations with different action profiles are desired and requested by the patients. One patient may, on the same day, use insulin formulations with very different action profiles. The action profile requested is, for example, depending on the time of the day and the amount and composition of any meal eaten by the patient.

There is a big need for insulin formulations with different profiles of release of insulin. A patient may, during the day, use insulin formulations with different profiles of release. For example, the patient may, before a meal, use a fast-acting insulin formulation with no retarded action. Another patient may, before a meal, use a formulation having both a fast action and a retarded action. In such a formulation having both a fast action and a retarded action, the ratio between fast action and retarded action may vary considerably. Before a patient goes to sleep, the patient may use a long-acting insulin formulation. Some patients will, before they go to sleep, use a formulation having both a fast action and a retarded action.

It is a goal of the present invention to provide stable insulin/betaine pharmaceutical combinations and/or dosages forms suitable to meet patients' needs. Such insulin/betaine combinations are suitable for reducing the necessity of repeated administrations when rapidly and for long periods of time controlling blood glucose in a mammal.

Diabetic conditions are generally classified as either insulin-dependent diabetes mellitus (IDDM, Type I diabetes) or non-insulin-dependent diabetes mellitus (NIDDM, Type II diabetes). There are also less common clinical pathologies that are associated with diabetic conditions, such as gestational maturity-onset diabetes of youth (MODY), tropical diabetes secondary to chronic pancreatitis, diabetes secondary to pancreatic disease or surgery, and diabetes secondary to endocrinopathies.

The concept of combination therapy is well exploited in current medical practice. Treatment of pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination might be approximately equal to the sum of the effects of each drug alone), but in other cases the effect can be synergistic (the efficacy of the combination is greater than the sum of the effects of each drug given alone). In real medical practice, it is often quite difficult to determine if drug combinations are additive or synergistic.

For most diabetic patients, treatment involves some form of insulin therapy. In addition, IDDM patients may receive a biguanide (e.g., metformin) to enhance the insulin utilization by peripheral tissues. NIDDM patients are often treated with a combination of insulin, a sulfonylurea (to enhance insulin production in the pancreas) and a biguanide or glitazone (to enhance insulin sensitivity by peripheral tissues). For example, the improved utility of a glitazone in combination with a sulfonylurea was recently demonstrated in human clinical trials (see, WO 98/36755). Recently, two glitazone compounds (rosiglitazone and pioglitazone) were approved in the United States for the treatment of NIDDM patients in combination with metformin.

A variety of antidiabetic compounds are known. For example, sulfonylureas are a group of drugs that induce hypoglycemia by stimulating insulin release from the pancreas. Generally, sulfonylureas have found wide utility in the treatment of NIDDM. Their efficacy is decreased in IDDM because of the inherent inability of the patient to produce insulin. Adverse reactions to sulfonylureas occur in a fraction of patients, particularly the elderly. One of the most severe side effects is hypoglycemia and coma. Other side effects include nausea and vomiting, cholestatic jaundice, agranulocytosis, cardiovascular mortality, aplastic and hemolytic anemias, generalized hypersensitivity reactions and dermatological reactions.

Biguanides are another group of drugs, first introduced in the mid 1950's that have shown efficacy in the treatment of hyperglycemia by mechanisms that are not well understood. The best known agents of this type include metformin, phenformin and buformin. Unlike the sulfonylureas, metformin does not induce release of insulin from the pancreas. It is thought that its effects are mediated by increasing insulin activity in peripheral tissues, reducing hepatic glucose output due to inhibition of gluconeogenesis and reducing the absorption of glucose from the intestine. Side effects associated with the use of biguanides include lactic acidosis, diarrhea, nausea, and anorexia. These agents are often given in combination with drugs that increase the output of insulin from the pancreas, such as the sulfonylureas, which sometimes results in greater efficacy and/or the ability to use lower doses of the drugs, with an improved side effect profile.

More recently, the glitazones have been introduced and are widely used in the treatment of NIDDM. These agents, also known generically as thiazolidinediones, such as troglitazone, rosiglitazone and pioglitazone, are thought to work by increasing the sensitivity of peripheral tissues, such as skeletal muscle, towards insulin. They are often used in combination with insulin or other agents, such as the sulfonylureas, that enhance the release of insulin from the pancreas. A number of side effects have been described during the clinical evaluation of these agents, including hepatotoxicity, organomegaly, edema, anemia and body weight gain. While hepatotoxicity may be the most acutely life-threatening of these conditions, it does not appear in a large percentage of the patient population. On the other hand, the increases in body weight gain associated with chronic glitazone treatment are generally perceived as worsening an already critical co-morbid condition in the majority of the diabetic patients, and may ultimately result in the loss of antidiabetic efficacy for this type of agent after chronic treatment.

Alpha.-Glucosidase inhibitors, such as acarbose, reduce intestinal absorption of starch, dextrin, and disaccharides by inhibiting the action of intestinal brush border .alpha.-glucosidase. Inhibition of this enzyme slows the absorption of carbohydrates and the rise in plasma glucose that normally follows after a meal is blunted. Acarbose has shown some benefit in IDDM and NIDDM patients, but is often associated with dose-related malabsorption, flatulence and abdominal bloating.

Other types of agents that have found limited utility in treating diabetes include potassium channel antagonists such as repaglinide, and aldose reductase inhibitors such as zopolrestat and tolrestat. Still in the experimental stage, glucagon antagonists, activators of the retinoid-X receptor (RXR), activators of PPAR.alpha., activators of PPAR.delta. and anti-obesity agents are also being evaluated as potential antidiabetic agents.

In view of the foregoing, there remains a need in the art to provide more efficacious treatment for diabetic conditions and diabetic complications. Combination therapy treatments are needed that will reduce the amount of drugs taken, thereby decreasing side effects. Surprisingly it was found that combining the betaines, i.e. one or more compounds selected from one or more of betaines, lipidic betaines, betaine lipids, of the invention with insulin agents enhance their effectiveness, the duration of theirs effects while lessening their potential side effects. The concomitant uses of betaines with insulins agents permit to lower the amounts of the latter while augmenting their half-life. The present invention fulfils these and other needs.

SUMMARY OF THE INVENTION

The present invention provides pharmaceutical compositions for the treatment of a variety of diseases, including diabetes mellitus, such as IDDM, NIDDM, gestational diabetes, juvenile diabetes, and the like, using combination therapy. In certain aspects, the pharmaceutical compositions comprise a pharmaceutically acceptable carrier with a compound of Formula I and an insulin agent and/or compound favorising the production of insulin by the body. Surprisingly, Betaine combination with insulin extends the half life of insulin and augments its efficiency and/or its bioavaibility. Advantageously, the compositions of the present invention provide clinical advantage over the use of a single agent alone. As such, the present advantageous invention provides a combination or association or composition comprising:

I) a compound of Formula I $(CH_3)_3N^+—(CH_2)n-COO^-$) n being an integer from 1 to 5 (preferably n=1) including pharmaceutically acceptable salts of compounds of Formula I, esters thereof, precursors thereof, and mixtures thereof; and II) one or more insulin agents, including, but not limited to, insulin therapy, short acting insulins, medium acting insulins, long acting insulins, prodrugs thereof, mixtures thereof or theirs pharmaceutically acceptable salts, and possibly, but advantageously, at least a pharmaceutically acceptable carrier or diluent.

In certain aspects, the compositions of the present invention comprise a compound of Formula I formulated together with one or more insulin agents. Alternatively, the compositions of the present invention comprise a compound of Formula I independently formulated with one or more insulin agents i.e., separately formulated.

In one embodiment, the combinations of the invention can further comprise one or more antidiabetic agents including, but not limited to, sulfonylureas, biguanides, glitazones and other PPAR.gamma. agonists, .alpha.-glucosidase inhibitors, potassium channel antagonists, aldose reductase inhibitors, glucagon antagonists, activators of RXR, activators of PPAR.alpha., activators of PPAR.delta., or anti-obesity agents.

The pharmaceutical methods of treatment, combinations and uses of compounds of formula I, i.e. betaines, with insulins are claimed. Such insulin agents can comprise all forms of insulins known by the skilled in the art, such as short acting insulins, medium acting insulins, long acting insulins selected, their pharmaceutical forms or their mixtures selected from the group consisting of Humalog, Novorapid, Novorapid Novolet, Lantus, Long-acting analogues, Levemir, Human Actrapid, Human Velosulin, Pork Actrapid, Humaject S, Humulin S, Hypurin Bovine Neutral, Hypurin Porcine Neutral, Insuman Rapid, Insuman Rapid Opti Set, Medium and long-acting, Humulin I, Humulin Lente, Humulin ZN, Human Insulatard, Human Monotard, Pork Insulatard, Human Ultratard, Hypurin Bovine Isophane, Hypurin Bovine Lente, Hypurin Bovine Protamine Zinc, Hypurin Porcine Isophane, Insuman Basal, Insuman Basal OptiSet, Analogue mixtures, Humalog Mix, NovoMix, Mixtures, Humaject, Human Mixtard, Pork Mixtard, Hypurin Porcine Isophane mix, Insuman Comb, Insuman Comb OptiSet and their mixtures.

Thus the present specification describes the administration of a composition or combination comprising:
i) One or more compound of Formula I (preferably glycine betaine), which increase insulin production and/or effectiveness and/or body half-life and/or increase peripheral tissue sensitivity to insulin, with
ii) an antidiabetic agent such as insulin therapy, or a stimulator of insulin secretion, and the like, increases the efficacy of either agent alone. In addition to increased efficacy, the combination therapy of the present invention allows for a concomitant reduction in the dose of the agents. The combination therapy of a compound of Formula I and one or more of another antidiabetic agents (e.g., biguanides, glitazones, RXR ligands, PPAR.gamma. agonists, etc.) results in a reduction in the side effects normally associated with certain antidiabetic agents.

In certain aspects, the combination compounds of the invention are administered successively (for example prior to the administration of the antidiabetic agent) or substantially simultaneously in combination with antidiabetic agents that are ineffective for stimulation of insulin secretion or insulin sensitivity, such as a-glucosidase inhibitors, potassium channel antagonists, aldose reductase inhibitors, glucagon antagonists, RXR ligands, PPAR.alpha. agonists, PPAR.delta. agonists, and anti-obesity agents. Surprisingly, these types of combination therapy result in enhanced efficacy relative to the use of the single agents alone.

In another embodiment, the present invention provides methods of treating metabolic or inflammatory disorders in a host by administering a composition of the present invention. In certain preferred aspects, the method includes the administration of a composition comprising a combination of a compound of Formula I with the insulin agents delivered in a simultaneous manner, such as in a single formulation. In certain other aspects, the methods of the present invention include combination therapy wherein the compound of Formula I is administered at least partly first for example by means of a first formulation, followed by the insulin agent administration for example by means of another or separate formulation. The methods also include an antidiabetic agent, such as the insulins known and/or prescribed by the skilled person, being delivered first in one formulation, followed by a compound of Formula I in a separate formulation, for example in one or more separate compartment, form, dosage form, such forms suitable for administration according to different paths. The combination therapies, methods of treatment and/or dosages forms can be suitable for example for different routes of administration. For example all the administration forms and/or routes known and applied in clinical settings can be used according to the present invention. Such routes including, but not limited to, oral, dermal, transdermal, subcutaneous, parenteral, intraperitoneal, sublingual, nasal, pulmonary, rectal and theirs combinations. The present invention includes all such methods of administration. The combination therapy is especially efficacious on conditions associated with diabetes, such as obesity, cardiovascular diseases, cerebrovascular diseases, thrombosis, ischemia, hypoxia, hypertension, hypercholesterolemia, lipid disorders, peripheral neuropathies and other neurological disorders, and the like. The compound of formula I and the insulin agent can be administered simultaneously, but preferably with a controlled release at least partly for the amount to be administered for the compound of formula I and/or for the amount of antidiabetic agent.

DEFINITIONS

Betaine or betaines as used in the claims mean "Betaines" such as compound of formula I, "lipidic betaines" and "betaine lipids", as well as combinations and mixtures thereof.

The term "Betaines" as employed herein refers advantageously to compounds of formula $(CH_3)_3N^+(CH_2)_nCOO^-$ with n an integer from 1 to 5, (preferably glycine betaine n=1), pharmaceutically acceptable salts thereof esters thereof, precursors thereof, and mixtures thereof.

The terms "lipidic betaines" and "betaine lipids" refer to betaine lipids which are structural components of membranes commonly found in ferns, mosses, fungi, amoeba, eukaryotes such as nonseed plants and algae. Betaine lipids are ether-linked, non-phosphorous glycerolipids that resemble the more commonly known phosphatidylcholine in overall structure. Most common glycerolipids are containing a diacylglycerol moiety to which a polar head group is attached. This head group can be a carbohydrate moiety as in the very abundant plant galactolipids or a phosphorylester as in the glycerophospholipids, the most common lipid class in animals. Betaine lipids represent a third class of glycerolipids in which a quaternary amine alcohol is bound in an ether linkage to the diacylglycerol moiety. They can be obtained by extraction, by biosynthesis or by synthesis. The betaine lipid diacylglyceryl-O-4'-(N,N,N-trimethyl)homoserine and a closely related isoform diacylglyceryl-O-2'-(hydroxymethyl)(N,N,N-trimethyl)-β-alanine are the most common.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological, such as for example dissolution in aqueous media, conditions to provide the compounds of the present invention. Additionally, prodrugs can be converted to the compounds of the present invention by in vivo, chemical or biochemical methods in an ex vivo environment. For example, prodrugs can be slowly converted to the compounds of the present invention when placed in a reservoir such as transdermal patch and/or enteral reservoir and/or an implantable reservoir with a suitable enzyme or chemical reagent.

Certain compounds of the present invention can exist in un-solvated forms as well as solvated forms, including hydrated forms. In general, the solvated forms are equivalent to un-solvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can also contain unnatural proportions of atomic isotopes, stable isotopes etc., at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "prodrug" refers to compounds that are drug precursors, which, following administration, release the drug in vivo via a chemical or physiological process (e.g., a prodrug on being brought to the physiological pH is converted to the desired drug form).

"A combination amount sufficient," "an effective combination amount" "therapeutically effective combination amount" or "an effective amount of the combination of" all refer to a combined amount of both a compound of Formula I and the antidiabetic agent that is effective to ameliorate symptoms associated with diabetic diseases. As used herein, the term "combination" of compound of Formula I with an antidiabetic agent means the two compounds can be delivered in a simultaneous manner, in combination therapy wherein the compound of Formula I is administered first, followed by the antidiabetic agent, as well as wherein the antidiabetic agent is delivered first, followed by a compound of Formula I. The desired result can be either a subjective relief of a symptom(s) or an objectively identifiable improvement in the recipient of the dosage.

The terms "synergistic effective amount" refers to a combined amount of both a compound of Formula I and an antidiabetic agent that is effective to cause a synergistic effect. Synergy is a biological phenomenon, in which the effectiveness of two active components in a mixture is more than additive, i.e., the effectiveness is greater than the equivalent concentration of either component alone. In certain aspects, the effectiveness of the combination therapy of a compound of Formula I and an antidiabetic agent is synergistic. Thus, synergism is a result, or function, that is more than the sum of the results, or functions of individual elements.

The term "simultaneous manner" and "combination treatment" refer to an administration protocol wherein the compounds of the present invention, and optionally at least further one antidiabetic agent, are administered within a single 24-hour period, 48 hours, 72 hours, 96 hours or more.

Onset of action: The length of time before insulin reaches the bloodstream and begins lowering blood glucose.

Peak time: The time during which insulin is at its maximum strength in terms of lowering blood glucose levels.

Duration of action: How long the insulin continues to lower blood glucose.

In one embodiment the period can be longer such as a week, a month, 3 months, 6 months, etc. Such longer periods are necessary when the compounds of the invention are administrated with implanted mini-pumps and/or devices and/or dosages forms suitable for long period deliveries in the body.

DETAILED DESCRIPTION OF THE INVENTION AND PREFERRED EMBODIMENTS

Compositions

Figure 1:
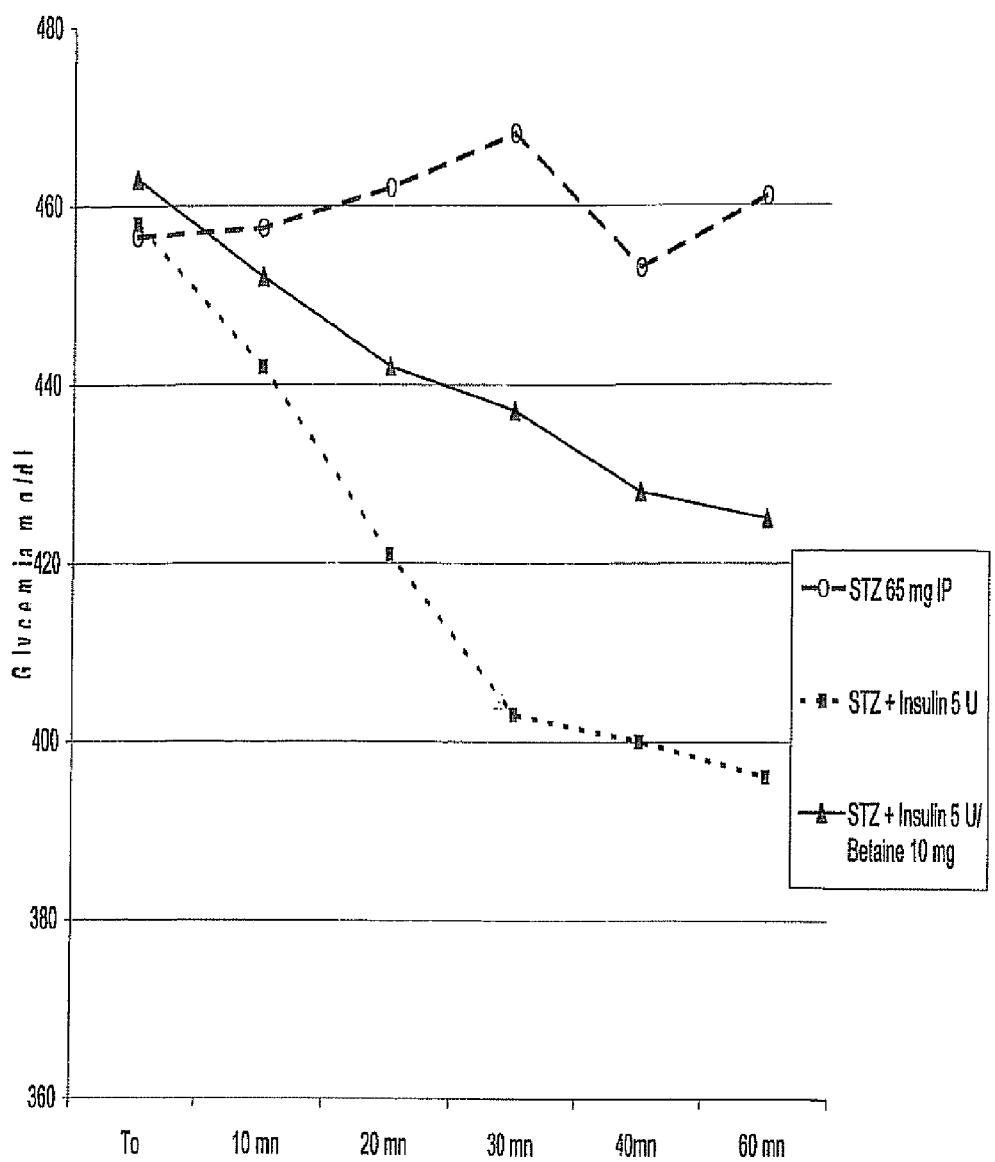
FIG. 1 is a graph of the results from Example 1, and depicts the change in blood glucose levels over time of rats injected with various insulin and insulin/betaine combinations.

In one embodiment, the present invention provides a pharmaceutical composition comprising:
(i) a compound of Formula I, preferably glycine betaine, and
(ii) an antidiabetic agent. Advantageously, the compositions of the present invention provide clinical advantage over the use of a single agent alone.

The invention relates thus to a pharmaceutical association or combination comprising a therapeutic effective amount of insulin or insulin analogue, and a therapeutic effective amount of a pharmaceutically acceptable betaine, in which the insulin and the betaine possibly form a chemical entity or complex, and in which the amount of betaine is adapted for controlling the degradation of the insulin or insulin analogue.

Advantageously, the amount of betaine is adapted for reducing the time of onset of action of the insulin after its administration of at least 30 minutes, preferably at least 1 hour, most preferably at least two hours. The time of onset action is advantageously the time required after administration for reaching a reduction of 30% preferably a reduction of 50%, most preferably a reduction of 70%) of the glucose content in the blood of a human suffering from diabetes, such as diabetes 1 and diabetes 2.

Preferably, the amount of betaine is adapted for increasing the efficiency of the insulin at least for the period of 4 to 6 hours after administration of the insulin, preferably for the period of 3 to 8 hours after administration of the insulin. The insulin is suitable for lowering the blood glucose content to about the blood glucose content of a human not suffering from diabetes for the period of 4 to 6, advantageously 4 to 8, most preferably 4 to 10 hours after administration, such as from 3 to 8 hours after administration.

According to an embodiment, the amount of betaine is adapted for increasing the in vivo bioavaibility of the insulin of at least 20%, preferably at least 30%, most preferably at least 50% for the period of 2 to 10 hours after administration. The bioavaibility or bioefficacy is increased by at least 20%, advantageously at least 40%, preferably at least 50% with respect to the bioavaibility or bioefficacy of the insulin used without betaine. While tests have still to be performed, possible mechanisms why a higher insulin bioavailability or bioefficacy can be reached is a lower degradation rate for insulin, a protecting effect by the betaine for sites or cells known to favor the degradation of insulin, activation of PPAR receptor by the betaine, whereby improving the control of the transcription of many genes in lipid catabolism, as well as the control of the expression of genes involved in adipocyte differentiation and insulin sensitization, improvement of the β-oxidation and insulin sensitization.

The insulin is advantageously an insulin known as a short acting insulin as such, whereby the amount of betaine is preferably adapted so as to achieve a rapid and efficient action of the insulin, as well as a prolonged action of insulin, meaning therefore a better efficiency of the insulin or that the amount of insulin can be reduce while enabling an effective treatment.

According to another embodiment, the insulin is an insulin or insulin mixture known as a mix of two different insulins, advantageously a mix selected from the group consisting of a mix of short acting insulin and long acting insulin, a mix of short acting insulin and intermediate acting insulin, a mix of intermediate acting insulin and long acting insulin, and a mix of short acting insulin, intermediate acting insulin and long acting insulin.

The insulin can also be an insulin known as a long acting insulin as such or an insulin known as an intermediate acting insulin as such.

The pharmaceutical association or combination of the invention is for example an association or combination comprising short acting insulin selected from the group consisting of regular insulin, insulin lispro, insulin analogues and a pharmaceutically acceptable betaine, (the insulin and betaine forming possibly a complex or a compound. In such a case the betaine content is expressed as also containing the betaine portion of the compound, while the short insulin content is expressed so as to also comprise the insulin portion of the compound) characterized in that its onset of action is sensibly equal to the pharmaceutical duration of activity is at least 1.3 the duration of activity of the pharmaceutically acceptable insulin.

Based on the unique features of the compounds of Formula I, the combination of one of these compounds with one or more antidiabetic agents described herein provides a significant clinical advantage over the use of a single agent alone. Thus, (1) the combination of a compound of Formula I (which is thought to increase peripheral tissue sensitivity to insulin) with either insulin therapy, or a stimulator of insulin secretion (e.g., a sulfonylurea) increases the efficacy of either agent alone, and moreover, allows for the reduction in dosage of all agents used in the combination therapy. In addition, (2) the combination therapy between a compound of Formula I and one or more other agents that increase insulin sensitivity (e.g., biguanides, glitazones, RXR ligands, PPAR.gamma. agonists, and the like), results in an enhanced effect between the various agents, with reduction in the side effects normally associated with these other agents. Further, (3) compounds of Formula I can be administered in combination with antidiabetic agents whose mode of action is other than stimulation of insulin secretion or insulin sensitivity (e.g., alpha.-glucosidase inhibitors, potassium channel antagonists, aldose reductase inhibitors, glucagon antagonists, RXR ligands and anti-obesity agents). Importantly, these types of combinations result in enhanced efficacy relative to the use of a single agent alone. In addition, the present invention includes (4) a combination treatment comprising a compound of Formula I (preferably glycine betaine) in combination with agents aimed at treating any one of the conditions often associated with diabetes, such as obesity, cardiovascular diseases, cerebrovascular diseases, thrombosis, ischemia, hypoxia, hypertension, hypercholesterolemia and other lipid disorders, peripheral neuropathies and other neurological disorders. Furthermore, (5) the combination therapy between a compound of Formula I and one or more other agents that increase insulin sensitivity (e.g., biguanides, glitazones, RXR ligands, PPAR.gamma. agonists, and the like), results in a prevention of diabetic troubles or conditions or in a delaying of the appearance of diabetic troubles or conditions.

The compounds of Formula I, particularly glycine betaine, are known to possess antiaggregant, anticoagulant, anti-adhesives, anti-inflammatory and fibrinolytic properties. The exact potency and intrinsic agonist activity of each compound of Formula I is a function of the compound's structure in a relatively predictable manner.

In an embodiment of the invention the compounds of Formula I, preferably glycine betaine (n=1) can be used for therapeutic and/or dietary supplementation as to manage diabetes.

According to the invention, therapeutic and/or dietary betaines supplementation may represent a potentially useful strategy for the management of diabetes. Betaine is a stable amino acid in an aqueous solution, and is not destroyed by sterilization conditions (e.g., high temperature and high pressure). In addition, betaine is nontoxic, and its administration is generally safe for both humans and animals. Betaine can be useful in the treatment of patients with type I diabetes, when been used along with insulin therapy to increase insulin secretion by the remaining pancreatic B-cells and improve insulin sensitivity in tissues via enhanced production of NO. This can help reduce the dosage and frequency of insulin therapy for patients with type I diabetes, while improving protein balance and endothelial function. In patients with type II diabetes, the pancreas is exhausted from the overproduction of insulin to overcome the insulin resistance of tissues, and most clinicians do not use drugs or agents that stimulate insulin secretion to treat this type of diabetes.

In one embodiment, one or more compounds of Formula I can be partly or completely in slow, delayed, extended, sustained or controlled release dosage forms when associated to one or more of the insulin compounds.

In one embodiment, one or more of the anti-diabetics compounds can be partly or completely in slow, delayed, extended, sustained or controlled release dosage forms when associated to one or more compounds of Formula I.

In one embodiment, one or more compounds of Formula I can be partly or completely in slow, delayed, extended, sustained or controlled release dosage forms and are associated to one or more anti-diabetics compounds which are partly or completely in slow, delayed or controlled release dosage forms.

Preferred compound of Formula I are those in which n=1 is i.e. glycine betaine and its pharmaceutical acceptable salts. But at least one or more of the betaines of Formula I can be used according to the invention alone to achieve the therapeutical purposes of the invention. One or more of the betaines of Formula I, can also be used in mixtures or in combinations with the insulin compounds of the invention to achieve the therapeutical purposes of the invention.

The combined compositions and methods of treatment of the present invention can further comprise one or more antidiabetic compounds. A wide range of antidiabetic agents can be used in the compositions and methods of the present invention. Suitable agents include, but are not limited to, one or more antidiabetic agent such as sulfonylureas, biguanides, glitazones and other PPAR.gamma. agonists, alpha.-glucosidase inhibitors, potassium channel antagonists, aldose reductase inhibitors, glucagon antagonists, activators of RXR, insulin therapy or other anti-obesity agent, prodrugs thereof, or pharmaceutically acceptable salts of the antidiabetic agents. In certain instances, the antidiabetic agents include, but are not limited to, one or more agents such as sulfonylureas and analogs, including, but not limited to, chlorpropamide, glibenclamide, tolbutamide, tolazamide, acetohexamide, glipizide, glimepiride, repaglinide and meglitinide; biguanides, including, but not limited to, metformin, phenformin and buformin. The methods of treatment combining the uses of one or more of the antidiabetic agents, as described in the present application, with the combined compounds of the invention for treating the pathologies, as described in the present application, are also claimed.

In one embodiment, the combined compounds of the invention are claimed to treat, alleviate and/or provide method of treatment to diabetic associated conditions such as: diabetic retinopathy, heart disease, mouth conditions, proteinuria, retinal detachment, transient ischemic attack, hypertension, pulmonary hypertension, portal hypertension, obesity, high cholesterol, diabetic retinopathy, heart disease, etc.

In one embodiment, the associations of the present application can be further associated and/or combined with one or more therapeutic agent selected from the group consisting in: aspirin, polyphenols, vitamins, Dhea, statins, bi-aspirin, antioxidants, anti-cholesterol agents, etc.

In another embodiment, the insulin agents include various forms of insulin, such as insulin in its various dosage forms, subcutaneous, oral, inhaled, sublingual, and the like, molecular variations, and short-, medium- and long-acting versions. Suitable insulin sources include, but are not limited to, recombinant human insulin, natural pig insulin, natural ox insulin, natural bovine insulin, natural human insulin, recombinant human argine-insulin, recombinant human aspartic-insulin, dalanated insulin, defalan insulin, glargine insulin, human insulin zinc, human insulin isophane, lispro insulin, neutral insulin, human proinsulin, their mixtures and the like.

Methods, Uses, Dosages and Schedules

In another embodiment, the present invention provides a method for modulating conditions associated with diabetes or diabetes-related disorders in a host, comprising administering to the host an efficacious amount of compositions comprising (i) a compound of Formula I in combination with (ii) one or more insulin agents.

The pharmaceutical compositions of the present invention are suitable for use in a variety of drug delivery systems. Examples of suitable formulations for use in the present invention are found in Remington's Pharmaceutical Sciences (Mack Publishing Company, Philadelphia, Pa., 17th ed. (1985), which is incorporated herein by reference. In addition, for a brief review of methods for drug delivery, see, Langer, Science 249:1527-1533 (1990), which is incorporated herein by reference.

The pharmaceutical compositions of the present invention are intended for subcutaneous, intraperitoneal, lingual, sublingual, nasal, pulmonary, parenteral, topical, oral or local administration. In certain aspects, the pharmaceutical compositions are administered parenterally, e.g., intravenously, subcutaneously, intradermally, or intramuscularly. In one embodiment, the invention provides compositions for parenteral administration which comprise a compound of Formula I, one or more insulin agent as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration.

Additionally the compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid formulations, compounds of Formula I can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

In one embodiment the invention claims entrapped insulins/betaines in microcapsules and or nanocapsules.

In one embodiment the invention claims entrapped insulins/betaines in microspheres and or nanospheres.

In one embodiment the invention claims entrapped insulins/betaines in liposomes and/or in multiple liposomal formulations.

In one embodiment the invention claims the combinations insulins/betaines further combined with mucosal bioadhesives.

In one embodiment the invention claims the combinations insulins/betaines further combined with chitosan.

In one embodiment the invention claims the combinations insulins/betaines further combined with permeation enhancers.

In one embodiment the invention claims the combinations insulins/betaines in slow release and/or buoyant and/or floating dosages forms.

For aerosol administration, the compounds of Formula I and insulin agents are preferably supplied in finely divided form along with a surfactant and propellant. The surfactant must, of course, be nontoxic, and preferably soluble in the propellant. In one embodiment the betaines of the invention can be used as surfactants. Others representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The compounds of the present invention can be prepared and administered in a wide variety of oral, enteral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I or a pharmaceutically acceptable salt of a compound of Formula I.

For preparing pharmaceutical compositions from the compounds of the present invention, pharmaceutically acceptable carriers can be either solid or liquid. Solid oral form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from 5% to 95% of the active compounds. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active components in water and adding suitable colorants, flavors, stabilizers, preservatives and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate and/or effective quantities of the active components. The unit dosage form can be a packaged preparation, the package containing discrete quantities of preparation, such as blisters, pocketed tablets, capsules, and powders and/or beads in vials, bags, sachets, or ampoules. Also, the unit dosage form can be a capsule, tablet, cachet, or lozenge itself, or it can be the appropriate number of any of these in packaged form.

The pharmaceutical preparations/compositions of the invention can be suitable for pen injection (such as Novopen and similar devices).

The quantity of active insulin components in a unit dose preparation may be varied or adjusted from 0.1 mg to 100 mg, preferably 1.0 mg to 10 mg according to the particular application and the potency of the active component. The composition can, if desired, also contain other compatible therapeutic agents.

In therapeutic use especially for the treatment of IDDM, or inflammatory conditions, the insulin compounds utilized in the pharmaceutical methods and/or combinations of the invention are administered at the initial dosage of about 0.01 mg/kg to about 1 mg/kg daily. A daily dose range of about 0.01 mg/kg to about 0.5 mg/kg is preferred. Most preferably, the daily dose range is comprised between 0.02 mg/kg and 1 mg/kg, especially between 0.03 mg/kg and 0.5 mg/kg. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages that are less than the optimum dose of the compound. Thereafter, the dosage is increased by small increments until the optimum effect under circumstances is reached. For convenience, the total daily dosage may be divided and administered in portions during the day, if desired.

In therapeutic applications, the compounds of Formula I and antidiabetic agents of the present invention are administered to a patient in a combination amount sufficient to elicit a response. An amount adequate to accomplish this is defined as "therapeutically effective combination dose." The methods include the administration of the combination of compound of Formula I with antidiabetic agent wherein the two components are delivered in a simultaneous manner, in combination therapy wherein the compound of Formula I is administered first, followed by the antidiabetic agent, as well as wherein the antidiabetic agent is delivered first followed by the compound of Formula I.

The betaine of Formula I utilized in the pharmaceutical method of the invention is administered at the initial dosage of about 0.01 mg/kg to about 200 mg/kg daily. A daily dose range of about 0.1 mg/kg to about 100 mg/kg is preferred. Most preferably, the daily dose range is comprised between 1 mg/kg and 100 mg/kg, especially between 10 mg/kg and 50 mg/kg.

Since the present invention has an aspect that relates to a combination of active ingredients which can be administered separately, the invention also relates to combining separate pharmaceutical compositions in kit form. The kit comprises two separate pharmaceutical compositions: a compound of Formula I, a prodrug thereof or a pharmaceutically acceptable salt and a second compound such as an antidiabetic agent as described above. The kit comprises a container for containing the separate components such as a divided bottle or a divided foil packet, however, the separate components can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Effective combination amounts for various uses will depend on, for example, the particular insulin agent, the compound of Formula I employed, the manner of administration, the weight and general state of health of the patient, and the judgment of the prescribing physician. In one embodiment, composition or formulation to be administered will contain a quantity of a compound(s) according to Formula I in an amount effective to treat the disease/condition of the subject being treated. The amount of antidiabetic agent will depend in part on its chemical class.

In certain instances, administration of the compounds of Formula I can be via any method which provides systemic exposure to the compound of this invention, preferably to the muscle and fatty tissue. These methods include oral routes, enteral, parenteral, intraduodenal routes, etc. Generally, the compounds of the present invention are administered in single (e.g., once daily) or multiple doses. The compounds of the present invention are generally administered in the form of a pharmaceutical composition comprising at least one of the compounds of Formula I together with a pharmaceutically acceptable carrier or diluent. Thus, the compounds of this invention can be administered individually or together in any conventional oral, parenteral or transdermal dosage form.

For oral administration, a pharmaceutical composition and/or, according to the invention claimed, can take the form of solutions, suspensions, tablets, pills, capsules, microemulsions, micro or nanospheres, powders, and the like. Tablets containing combinations various excipients such as sodium citrate, calcium carbonate and calcium phosphate are employed along with various binders such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, colouring agents, emulsifying agents and/or suspending agents, as well as such diluents as water, ethanol, propylene glycol, glycerine and various like combinations thereof.

In one embodiment, the combined compounds in the form of a powder, granules, micro-granules, micro-spheres, nano-spheres, pellets and gels. The combined compounds can be in the form of a pharmaceutical unit dosage form said dosage form being selected from the group consisting of sachets, pouches, blisters and bags. Pharmaceutical unit dosage form of a composition containing at least a betaine, said dosage form being selected from the group consisting of sachets, pouches, blisters and bags, wherein the pharmaceutical unit dosage form is provided with moisture barrier property defined by an increase of weight of the composition of less than 1% after storage of the unit dosage form in sealed condition in an environment with a temperature of 38° C. and a relative humidity of 90% during 30 days.

Such individual sachet being possibly further submitted to an encrypting against counterfeiting and/or a notch to facilitate the tearing and/or the opening.

As MVTR stands for "Moisture Vapour Transmission Rate", a measure of the passage of gaseous $H_2O$ through a barrier, the pharmaceutical oral unitary dose of betaine in a sealed dosage form from the group consisting of sachets, bags, blisters and pouches in which the dosage form is at least partly flexible, water impermeable and characterized by a protective barrier by a MVTR value inferior to 0.1 g/m$^2$ at 38° C. and 90% relative humidity during 24 hours.

In one embodiment, the sizes of the betaines particles can be selected so as to absorb minimally the water (for instance from micronized particles to an optimal size particles allowing a minimal water intake). Optionally the particles (or the dosage form such as a sugar-coated pill could be further enveloped by a surfactant having good moisture barrier) can be sugar-coated and optionally such particles can be trapped in a gel or a polymer before being packaged in a selected MVTR container or pharmaceutical unit dosage form.

For example the coating or primary packaging material could be a laminate which is made up of 12 μm PET, 25 μm Alufoil and a 50 μm PE inner heat-seal layer. Further high quality and clarity of surface decoration might be realized by gravure reverse printing process.

The complete barrier requirement for this highly hygroscopic product (betaine after being dried, i.e. its liquid content partially or completely removed) could be provided by a laminate of PET, PE and Alufoil. The single 250 to 5000 mg doses are easy to tear open and safe for mouth contact. In this dosage form betaine can be taken directly by mouth without the need to dissolve in water. Some flavoring agents might be added to mask betaines taste by the way augmenting patients' compliance. Geometrical forms which augment the facility of use can be privileged.

In one embodiment a stick format of the sachet will be preferred as it uses a minimum amount of material in relation to the volume of its contents and further by reducing the bag surface it allows also to reduce the MVTR.

The dosage forms can be optimized according to selected combinations of MVTR, betaine doses, tensile strengths, sizes, forms, coefficients of friction. The initial rate of moisture of the betaines can also be selected and/or controlled so as to lower the other parameters (MVTR, etc) thus augmenting the compliance of the dosage form.

In one embodiment, the compounds of Formula I and/or the antidiabetic compounds and/or the combined compounds of the invention can be manufactured in formulations, forms and dosages forms such as those claimed in WO0051596, US 20020065320, WO02062322, US 20040033223, WO2004049095, WO2004091601, BE 2004/0364, PCT/BE 2004/00110, PCT/BE 2004/000163 of the inventor.

According to the invention it will be appreciated that the actual preferred course of therapy will vary according to, inter alia, the mode of administration of the compound of Formula I, the particular formulation of the antidiabetic agent being utilized, the mode of administration of the compounds, the particular disease being treated and the particular host being treated. The optimal course of therapy for a given set of conditions can be ascertained by those skilled in the art using conventional course of therapy determination tests and in view of the information set out herein.

Additional Uses for Compounds of Formula I

The compounds of Formula I have been recently shown to enhance nitric oxide production in human and other species. As such, specific compounds of Formula I are well suited for the treatment of the various conditions and diseases established to be mediated by, or linked to nitric oxide levels. Thus the compounds of Formula I can be suitable to treat below outline other indications alone or in combinations with the insulin compounds of the present invention.

Metabolic Conditions such as: Diabetes and Conditions Secondary to Diabetes, Hypertension, Angina pectoris, Dyslipidemia, Hypertriglyceridemia, Gout, Hyperlipoproteinemias, Hypercholesterolemia, Nephropathy and other renal diseases secondary to diabetes, Diabetic neuropathy, other insulin-resistance-related diseases, polycystic ovarian syndrome, glucocorticoid-induced insulin resistance.

Obesity, promote adipocyte differentiation and fat.

Hypertension, suppress or lower or cross endothelin-1 secretion by vascular endothelial cells and result in decreased blood pressure.

Lipid Disorders, been implicated in systemic glucose and lipid homeostasis.

Bone Disorders.

Female specific conditions where Formula I compounds can be used to inhibit excessive uterine bleeding in women and also to alleviate hormones disorders in menopausal women Male hormone disorders such as andropause related disorders.

Acne and other skin disorders associated with differentiation of epidermal cells as proliferative diseases of the skin.

CNS, Alzheimer's disease, Neuroinflammation, such as ischemic stroke, closed-head injury, and multiple sclerosis, Chemotherapy, Cancer.

Inflammation/Immune disorders.

Ophthalmic, Macular Degeneration

3. Anti-angiogenic

Additional Embodiments

In one embodiment Betaine is claimed to improve glucose tolerance.

Due to its very low toxicity betaine can be particularly suitable as therapeutic agent for treating and/or alleviating symptoms linked non insulin dependent gestational diabetes.

Due to its pharmacological capabilities betaines can be particularly suitable in methods of treatment combining betaine and pancreatic cells transplantation.

In one embodiment, the insulin/betaines combinations can be combined with the dialysis solutions before infusion. The diluted insulin/betaines solution will result in slow and continuous diffusion.

Contrarily to NPH insulin the mix do not precipitates and is rapidly absorbed across the peritoneal membrane, thus it is particularly suitable for peritoneal administrations. Insulin/betaines combinations are stable, soluble insulin formulations having both a fast and a long action, meaning by the way that Insulin/betaine combinations represent a controlled release or long acting dosage form which can be administrated intraperitoneally contrarily to Hagedorm insulin. Thus the combined forms of the invention are particularly suitable for pumps or implantable pumps which deliver therapeutical compound inside the living body.

In one embodiment the combinations of the invention can further comprise zinc and its physiological acceptable salts or derivatives.

The primary mechanism of action of betaine in lowering blood glucose appears to be dependent on stimulating the release of insulin from functioning pancreatic beta cells.

The present invention relates to methods for administration of insulin into the intradermal compartment of subject's skin, preferably to the dermal vasculature of the intradermal compartment. The methods and combined dosage forms of the present invention enhance the pharmacokinetic and pharmacodynamic parameters of insulin efficiency and/or delivery and/or duration of action and effectively result in a superior clinical efficacy in the treatment and/or prevention of diabetes mellitus. The methods of the instant invention provide an improved glycemic control of both non-fasting (i.e., postprandial) and fasting blood glucose levels and thus have an enhanced therapeutic efficacy in treatment, prevention and/or management of diabetes relative to traditional methods of insulin delivery, including subcutaneous insulin delivery.

The low efficiency of pulmonary delivery of the commercially available inhalation devices and the relatively low pulmonary bioavailability of insulin represent potential aerosol formulation and delivery barriers. The use of the H-MAP may increase the potential of the lungs as route of administration for insulin in concentrations required to treat diabetes.

In one embodiment, betaines due to their cationic structure might be covalently coupled to insulin, an anionic compound, to obtain derivatives that have a decreased receptor-binding capacity and thus avoids receptor-mediated degradation, thereby living longer in circulation. Thus, insulins might be modified by the addition of one or more betaine to produce a suspension of amorphous insulin. In one embodiment, insulins reacted with one or more betaine to form complex from which one or more insulin is slowly released.

The insulin constituent of the betaine insulin conjugate undergoes a slow, spontaneous activation in the circulatory system, manifesting a prolonged glucose-lowering action in vivo.

In one embodiment, betaine alone and/or the compositions of the invention are claimed to lower and/or to control glycemia hemoglobin in a mammal.

In one embodiment, betaine alone and/or the compositions of the invention are claimed to lower and/or to control glycated hemoglobin in a mammal.

In one embodiment, betaine alone and/or the compositions of the invention are claimed to lower and/or to control acidosis in a mammal.

In one embodiment, betaine alone and/or the compositions of the invention are claimed to lower and/or to control ketones in a mammal.

In one embodiment, betaine alone and/or the compositions of the invention are claimed to lower and/or to control ketoacidosis in a mammal.

In one embodiment, betaine alone and/or the compositions of the invention are claimed to treat and/or prevent glaucoma and/or open angle glaucoma in a mammal.

In one embodiment, betaine can be combined in specific dosage forms with Vanadium an oral insulin-mimetic agent that diminishes hyperglycemia, improves beta-cell insulin store and secretory function, and can reverse the diabetic state chronically.

In one embodiment betaine is used as an insulin sensitizer. Betaine might promote glucose entry to cells and thus possess pee se insulin like activity.

In one embodiment a slow release insulin consisting in a mix with betaine.

Betaine/insulin combinations provide more stable and more predictable glucose control and avoid micro-precipitation in the catheters due to better stability.

In one embodiment Betaine/insulin provide the possibility to be mixed with ultralente (very slow) insulins without affecting or being affected in their release and activity profile. Thus Betaine/insulin is compatible with other insulins and could be used in premixed formulations. Thus, it is provided an insulin formulation either possessing rapid onset of action and/or delayed or long acting action.

The present invention describes and claims premixed compositions where insulins/betaines mixtures are combined with insulins.

The betaines replacing protamine in the compositions of the invention.

In summary, subcutaneous administration of insulin suspended in betaine and/or betaine-insulin combinations, can bring about prolonged, non-hypoglycaemic glucose-lowering profiles, unattainable with insulin preparations, which are known to be active at the time of administration, But surprisingly the betaine-insulin combinations retain insulin short acting profile, while augmenting insulin efficiency and duration of action.

The goal of any insulin program is to keep blood sugar within or close to its normal range by mimicking normal pancreatic secretions of insulin. Ideally, this regimen would provide continuous (basal) secretion of insulin as well as periodic meal-related secretions. As useful as the current types of human insulin are, they're not perfect. Their action and rate of absorption vary. Thus the present invention provides dosage forms with onset and duration which resemble to those of natural (endogenous) insulin.

Several pharmacological problems complicate insulin therapy. Firstly, subcutaneous insulin injection sites drain into the peripheral, not the portal circulation.

Thus, insulin-treated patients can only achieve effective portal insulin concentrations at the expense of hyperinsulinemia in the systemic circulation. Secondly, the pharmacokinetic and pharmacodynamic properties of therapeutic insulin preparations are a poor match for the finely tuned β cell: 'short-acting' insulins are absorbed too slowly and last too long to mimic the normal prandial peaks while 'long-acting' preparations do not provide the steady, low concentrations required between meals. Moreover, subcutaneous insulin absorption is highly variable, so that the glucose-lowering effect of an insulin dose cannot be accurately predicted. Some of these pharmacokinetic shortcomings have been addressed by the development of the insulin compositions, described and claimed in the present invention.

The compositions of the invention can be administered by various routes, including intraperitoneal, infusion, pulmonary, nasal, oral, sub-lingual, cutaneously (patches), transcutaneously (with compressed air or any acceptable vehicle) and subcutaneous injections.

Thus the compositions of the invention mimic the physiological release of insulin in a mammal. In a preferred embodiment the compositions of the invention enhance insulins effectiveness and thus make possible to reduce the total amounts or doses of insulins administered daily or daily (24 hours) required in a patient or an animal in need.

In one embodiment, the compositions of the invention are suitable for treating patients suffering or having protamine induced antibodies.

In one embodiment, the betaines of the invention are claimed and are suitable for treating patients suffering or at risk to suffer from diabetes, said betaines having pharmacological effects by regulating $Na^+/K^+$ ATPases in said patients.

In an important embodiment, the betaines of the invention are claimed and are suitable for treating patients suffering or at risk to suffer from diabetes, said betaines having pharmacological effects by enhancing insulin secretion in said patients.

In an important embodiment, the betaines of the invention are claimed and are suitable for treating patients suffering or at risk to suffer from diabetes, said betaines having pharmacological effects by enhancing C-peptide secretion in said patients.

Insulin/betaine increases glucose disposal into muscle. In addition, in vivo insulin/betaine elicits distinct nitric oxide synthase-dependent vascular responses to increase total skeletal muscle blood flow and to recruit muscle capillaries by relaxing resistance and terminal arterioles, respectively.

In one embodiment the betaines are claimed to protect the insulins from enzymatic degradation follows receptor-mediated endocytosis.

The invention further relates to pharmaceutical formulations containing insulin and betaines, wherein insulin/betaine combinations have a profile of action which is identical or substantially identical with the profile of action of short and/or fast acting insulins combined to a profile of action of delayed and/or long acting insulins. The invention also relates to methods of treating diabetes which utilize the pharmaceutical formulations of the invention.

Insulin/betaine belongs to a new class of basal insulin analogues with a neutral pH and unique mechanism for prolonging action (protraction). Currently available basal insulin preparations may produce variable blood glucose responses to the same dose given on different days. The distinct chemical structure and/or formulations allow for a slower and more stable absorption from the injection site.

It is a goal of the present invention to provide stable insulin/betaine pharmaceutical combinations and/or dosages forms suitable to meet patients' needs. Such insulin/betaine combinations are suitable for reducing the necessity of repeated administrations when rapidly and for long periods of time controlling blood glucose in a mammal.

One object of the present invention is to furnish insulin/betaine formulations wherein the betaines and insulins have been co-crystallised together. All the methods, techniques and processes known by the skilled man previously used in the art to co-crystallise insulins with protamine are suitable in the scope of the present invention to be used to co-crystallise the betaines and insulins.

One object of the present invention is to furnish insulin analogs obtained by the addition of one or more betaine. Such analogs may vary with regard to their pharmacokinetic profile, stability, tissue specificity and mode of administration. In addition, alterations involving incorporation of betaines moieties in insulin and its co-crystallization with betaines are used to modulate the time-action profile of the drug and/or to modify the native insulin sequence.

In one embodiment the combinations of the invention, wherein the betaines and insulins are mixed and/or co-crystallised, are further submitted to one or more separation step selected from centrifugation, ultracentrifugation, chromatic separation, chemical separations, electrophoresis, filtration, ultrafiltration, nanofiltration, osmosis reverse and the processes generally used by the skilled man in insulins and/or betaine purifications.

In one embodiment the permeates and/or the retentates, and/or theirs combinations, of such separations processes can be used to obtain a medicament.

In another embodiment, the separation processes can be used to obtain particular insulins/betaines mixtures having the desired profiles such as, but non limited to: particular onsets of actions, particular durations of actions, particular modes of administrations, particular pharmacological effectiveness and the combinations of such profiles/characteristics. Accordingly, the separations steps/processes serve to modulate the desired characteristics of the combinations of the invention.

One object of the present invention is to furnish insulin/betaine formulations having a convenient profile of action.

In one embodiment the betaines are claimed to protect the insulins from enzymatic degradation follows receptor-mediated endocytosis Another object of the present invention is to provide soluble insulin/betaine formulations having both a fast onset of action and also a retarded action.

Another object of the present invention is to furnish insulin/betaine formulations having no or only a minor amount of non-dissolved material.

Another object of the present invention is to furnish insulin/betaine formulations containing both a fast and long acting insulin component wherein the two insulin components acts as or acts substantially as they would have acted if they had been the only insulin components present in the formulation.

Another object of the present invention is to furnish insulin/betaine formulations having a profile of release which is very predictable, both from time to time an also form patient to patient.

Another object of the present invention is to furnish combinations of betaines with short acting analogs, said combinations being further combined with short acting analogs. The ratios between short acting analogs and short acting analogs/betaines can vary from 1/10 to 10/1.

DETAILS OF THE INVENTION

The formulations of the inventions have no or only a minor content of non-dissolved material. The formulations of the present invention have a profile of release which is very predictable, both from time to time and also from patient to patient.

The pharmaceutical formulation of this invention may be prepared using the conventional techniques of the pharmaceutical industry which involves dissolving and mixing the pertinent ingredients as appropriate to give the desired end product.

An isotonic agent, a preservative, and, optionally, a buffer is added as required and the pH value of the solution is adjusted—if necessary—using an acid, for example, hydrochloric acid, or a base, for example, aqueous sodium hydroxide as needed. Finally, the volume of the solution is adjusted with water to give the desired concentration of the ingredients.

In a preferred embodiment of this invention, the formulation contains solely a glycine betaine as agent rendering the solution isotonic and optionally one or more agents selected from the group of antimicrobial preservative, a pH-buffering agent, and a suitable zinc salt.

In a preferred embodiment of this invention the compositions may content further a therapeutic active agent.

In a preferred embodiment of this invention, the formulation has a total amount of the insulin in the range from about 10 U/ml to about 1500 U/ml, preferably in the range from about 40 U/ml to about 1000 U/ml, more preferred in the range from about 100 U/ml to about 500 U/ml, for example, 100, 200, 400, or 500 U/ml. The term "U", when used herein, refers to insulin units. For insulin aspart, one unit equals 6 nmol (about 40 microgram) and for insulin detemir, one unit equals 24 nmol (about 160 microgram).

In a preferred embodiment of this invention, the preservative is phenol, m-cresol or a mixture of phenol and m-cresol. In a further preferred embodiment of this invention, the total concentration of phenol and/or m-cresol is in the range from about 20 mM to about 50 mM, preferably in the range from about 30 mM to about 45 mM. The concentration of phenol and/or m-cresol is, inter alia, dependent on the concentration of insulin.

In a preferred embodiment of this invention, the formulation has a content of zinc ions at the disposal of insulin in proportions in the range from about 2.3 to about 4.5 $Zn^{2+}$ per hexamer insulin (corresponding to from about 0.38 to about 0.75 $Zn^{2+}$/monomer insulin) where it is understood that the content of zinc is expressed per insulin hexamer as a theoretical value, i.e., as the number of zinc atoms per 6 molecules of monomeric insulin, independent of whether all insulin actually is present as hexameric insulin or not. The zinc salt used for preparing the formulations of this invention may, for example, be zinc chloride, zinc oxide or zinc acetate.

In a preferred embodiment of this invention, the isotonic agent is glycerol, mannitol, sorbitol or a mixture thereof at a concentration in the range from about 100 to 250 mM.

In another preferred embodiment of this invention, the formulation contains halogenide ions, preferably as sodium chloride, in an amount corresponding to from about 1 mM to about 100 mM, preferably from about 5 mM to about 40 mM. In a preferred embodiment of this invention, the pH buffer is sodium phosphate, TRIS (trometamol), N-glyeylglycine or L-arginine. Preferably, the pH buffer is a physiologically acceptable buffer in a concentration in the range from about 3 mM to about 20 mM, preferably from about 5 mM to about 15 mM. In a preferred embodiment of this invention, the formulations of this invention have a pH value in the range from about 7.0 to about 8.0.

In a preferred embodiment of this invention, the formulation of this invention has a content of non-dissolved material below about 0.1%, preferably below 0.01% (weight per weight).

Administration of the formulations of this invention may be via any route mown to be effective by the physician of ordinary skill. Parenteral and preferably subcutaneous administration is preferred.

The amount of the formulation of this invention that is administered to treat diabetes depends on a number of factors, among which are included the patient's sex, weight, physical activity, and age, diet of the patient, the underlying causes of the condition or disease to be treated, the route of administration and bioavailability, the persistence of the administered insulin or insulin analogues in the body, the specific formulation used, the potency of the insulin or insulin analogue used, a possible combination with other drugs, the severity of the case of diabetes, and the interval between dosages, if any interval. It is within the skill of the ordinary physician to titrate the dose and frequency of administration of the formulation of this invention to achieve the desired result. It is recommended that the daily dosage of the insulin components used in the formulation according to this invention be determined for each individual patient by those skilled in the art in a similar way as for known insulin compositions.

This invention is further illustrated by the following examples which, however, are not to be construed as limiting the scope of protection. The features disclosed in the foregoing description and in the following examples may, both separately and in any combination thereof, be material for realizing this invention in diverse forms thereof.

The invention will be described in greater detail by way of specific examples. The following examples are offered for illustrative purposes, and are not intended to limit the invention in any manner.

EXAMPLES

Example 1

Animal Model

Male Wistar rats (250 g) after 1 week stabulation are injected Streptozotocin 65 mg/kg intraperitoneally as to destroy pancreatic cells thus depriving the animals of endogenous insulin production. Rats were maintained at 24° C. under conditions of controlled lighting and were fed with normal chow and water ad libitum during 5 days. The experiment compounds, i.e. insulin (Bovine—Ref 15500 Sigma—U/kg) and Insulin/Betaine (U/mg/kg)+Insulin combination were injected subcutaneously at 1 ml/kg solutions to non-fastened rats at day of experiments. In Insulin/Betaine (U/mg/kg)+Insulin combination half of the Insulin was mixed with betaine, the second half being added after. Glycemia (mg/dl) was measured every 10 minutes using a glucometer One Touch Ultra—Johnson & Johnson. Blood samples for the analysis of blood glucose were taken from the tail veins. Groups consisted of five rats. (Control non diabetic animals displayed±140 mg/dl)

FIG. 1 shows the results of this test. Said figure gives the blood glucose level in function of the time, after the injection. IN means insulin units, while Betaine and BET mean glycine betaine (mg).

Example 2

The rats of example 1 were after the procedures of example 1, sampled every 2 hours using a glucometer One Touch Ultra—Johnson & Johnson. Blood samples for the analysis of blood glucose were taken from the tail veins.

Figure 2:
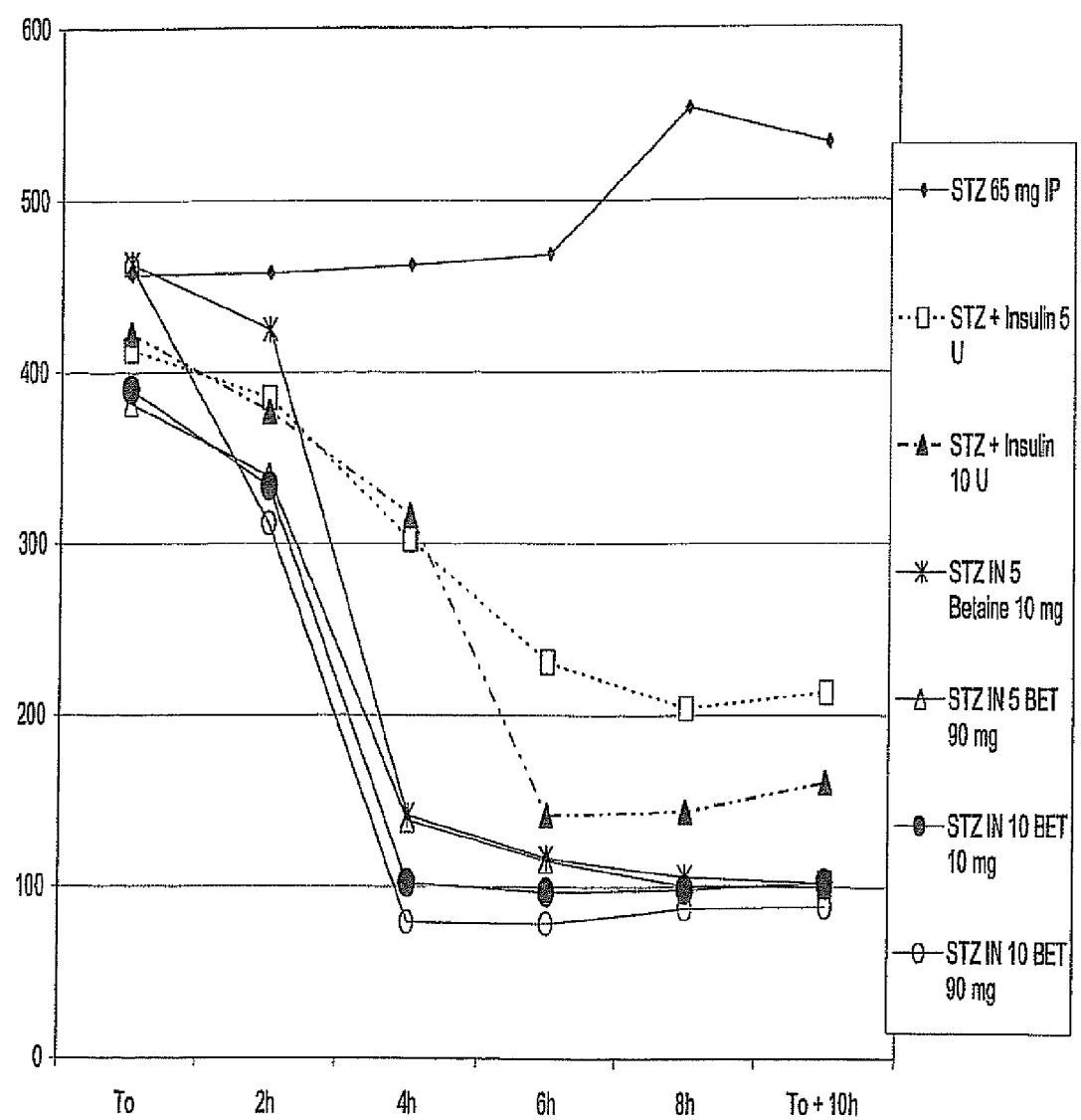
FIG. 2 is a graph of the results from Example 2, and depicts the change in blood glucose levels of the rats from Example 1, over an extended period of time.

FIG. 2 shows the results of this test. Said figure gives the blood glucose level in function of the time, after the injection. IN means insulin units, while Betaine and BET mean glycine betaine (mg). This figure clearly shows that by adapting the amount of betaine, it is possible to improve drastically the efficiency of the short acting insulin, said short acting having still a prolonged action up to after 10 hours.

Example 3

Male Wistar rats (±250 g) after 1 week stabulation are injected Streptozotocin 75 mg/kg intraperitoneally. Rats were maintained at 24° C. under conditions of controlled lighting and were feed with normal chow and water ad libitum during 5 days. The experiment compounds, i.e. insulin (Bovine—Ref 15500 Sigma—U/kg) and Insulin/Betaine (U/mg/kg) were injected subcutaneously at 1 ml/kg solutions to non-fastened rats at day of experiments. Glycemia (mg/dl) was measured every 2 hours using a glucometer One Touch Ultra—Johnson & Johnson. Blood samples for the analysis of blood glucose were taken from the tail veins. Groups consisted of five rats. High values (HI display on the device) were considered as 600 mg/dl. (Control non diabetic animals displayed ±140 mg/dl)

Figure 3:
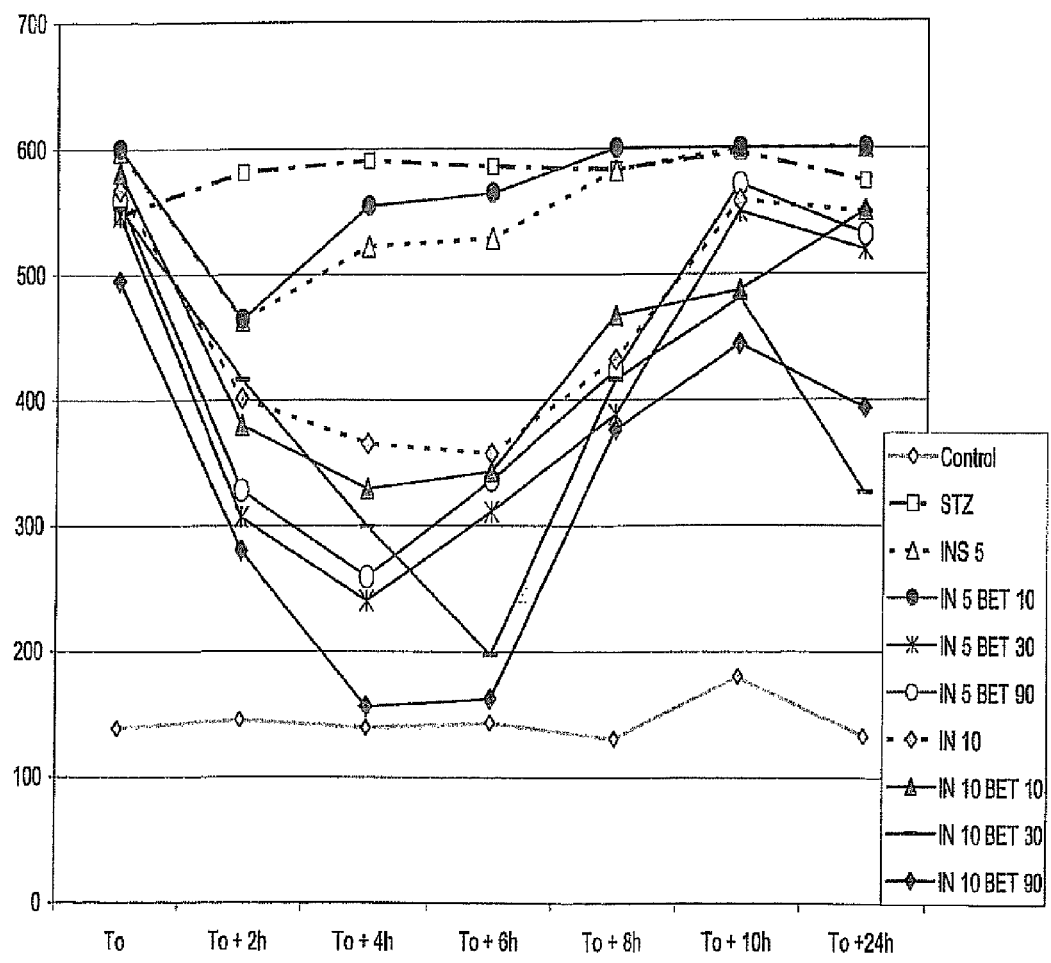
FIG. 3 is a graph of the results from Example 3, and depicts the change in blood glucose levels of rats injected with various insulin and insulin/betaine combinations in relation to a control group.

FIG. 3 shows the results of this test. Said figure gives the blood glucose level in function of the time, after the injection. IN means insulin units, while Betaine and BET mean glycine betaine (mg).

This figure shows clearly that by adapting the amount of betaine, it is possible to improve drastically the efficiency of the short acting insulin, said short acting having still a quick action, and a prolonged action up to after 24 hours, meaning that the short acting insulin is converted in a long acting insulin, for example an insulin active for about 24 hours or a daily insulin.

Example 4

Male Wistar rats (+250 g) after 1 week stabulation are injected Streptozotocin 60 mg/kg intraperitoneally. Animals (n=8/group) were fed with normal chow and water ad libitum during 5 days, then at day 1 (T0) Betaine (200 mg/kg/day) or placebo were dissolved and administrated daily in drinking water during 24 days; full access to normal chow was maintained during the whole experiments. Glycemia was measured morning at days of experiments, in non-fastened rats (as in previous exp.). At T0+7 days the treatments were inverted between the 2 groups.

Figure 4:
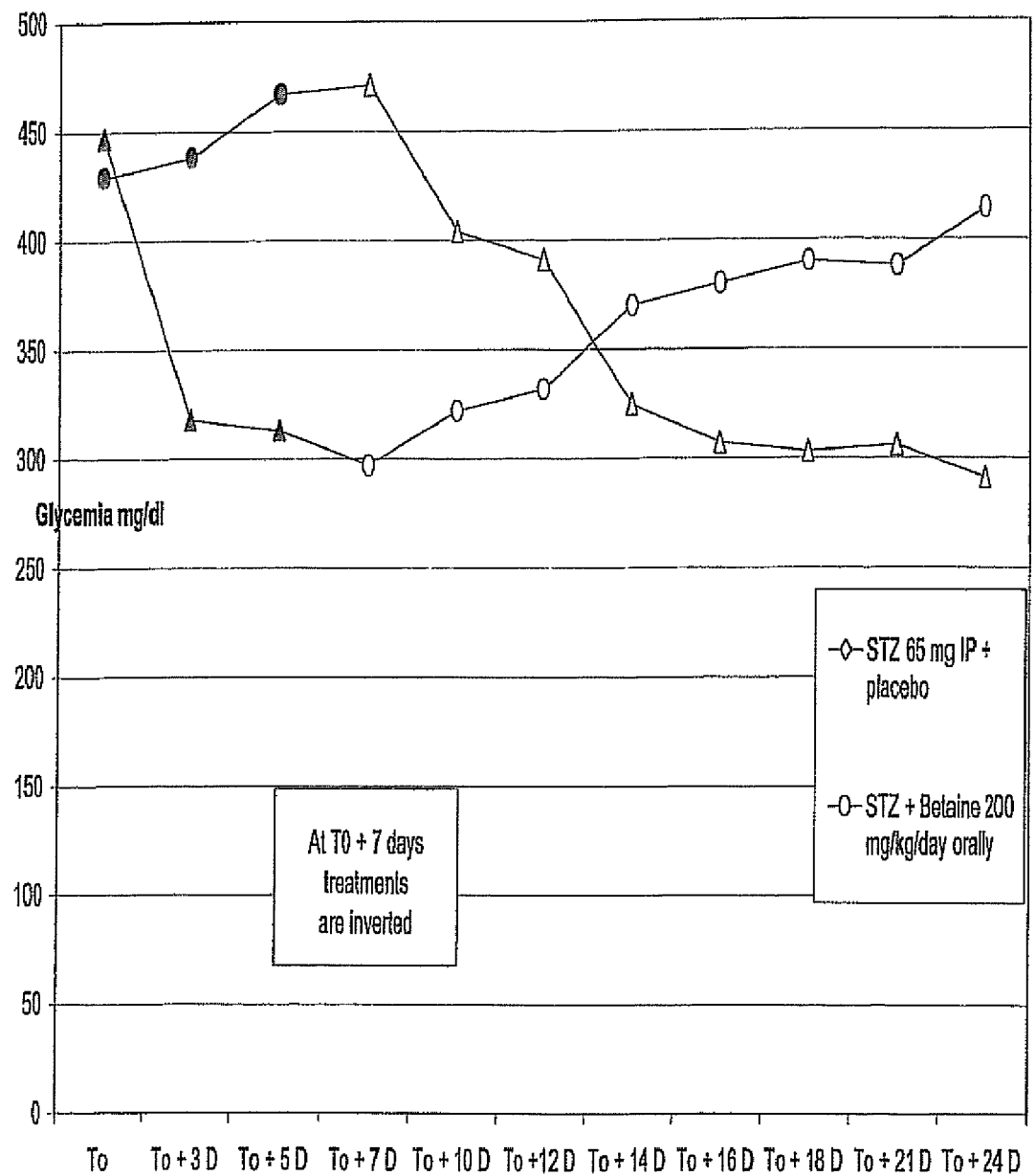
FIG. 4 is a graph of the results from Example 4, and depicts the blood glucose levels over a period of 24 days of rats fed betaine in their drinking water, in comparison to rats fed a placebo.

Results in FIG. 4 show that glycine betaine per se possesses an effect on the regulation of blood glucose and accordingly can be suitable to treat and/or to prevent diabetes pathological expressions in a patient in need.

Example 5

Dosage Form with Metformin and Betaine Anhydrous

Sachet comprising unit powder dosage form of 500 mg metformin and 2000 mg gycine betaine The dosage form of example 1 has been repeated excepted that metformin and glycine betaine are mixed together with a granulating agent, extruded and spheronized in beads of about 1 mm, The beads have been coated with eudragit, said eudragit being mixed in an organic solvent and sprayed on the beads, where after the beads are dried.

Example 6

This example illustrates combination therapy of a compound of Formula I and a metformin by oral administration.

Patients having NIDDM (Type II diabetes mellitus) are selected for therapy. The patients weigh between 70-100 kilograms. A compound of Formula I is orally administered in a dosage of 1 to 15 grams twice daily, more typically 100 mg/kg twice daily. For infants or children the doses suggested are lowered in a linear fashion based on body weight or surface area.

Half the patient population is administered metformin as well as a compound of Formula I using an effective dose of both agents. The other half of the patients are administered an effective dose of metformin. The patients are monitored for improvement in the manifestations of the disease and for side effects, such as body weight gain and signs of liver toxicity.

The combined compounds of the invention increased the patients' body's sensitivity to insulin and lowered glucose fasting levels.

The results indicate the administration of a combination of i) a compound of Formula I with ii) metformin increases the efficacy of either agent alone. The composition also provides concomitant decrease in the side effects of either agent alone.

Example 7

Capsule Containing Glyburide and Betaine Anhydrous

Sachet comprising unit powder dosage form of 1 mg metformin and 1000 mg glycine betaine Example 8

Solution of insulin was prepared, by using insulin composition similar to that marketed as injectable solution (such as intravenous or subcutaneous) to said insulin a solution of glycine betaine in sterile water was added. Prior to said mixing, the betaine solution was filtered.

The solution to be, sprayed/inhaled, before its mixing with betaine comprised from 50 to 500 insulin units/ml (short acting) equivalent to 2 mg to 20 mg.

The following table gives the content of the unit doses as 1.5 ml or 2 ml solutions for inhalation (nasal or pulmonary) having a pH of about 7.

Some of these solutions are balanced in their ratios as to be isotonic and are therefore suitable for subcutaneous/parenteral administrations. In a particular embodiment these solutions contain uniquely betaine as preferred agent used for achieving isotonicity.

| vial | Insulin (mg) | Glycine betaine (mg) |
|---|---|---|
| 1 | 10 | 50 |
| 2 | 10 | 100 |
| 3 | 7.5 | 100 |
| 4 | 2 | 30 |
| 5 | 5 | 100 |
| 6 | 4 | 30 |
| 7 | 4 | 35 |
| 8 | 4 | 100 |

-continued

| vial | Insulin (mg) | Glycine betaine (mg) |
|---|---|---|
| 9 | 10 | 200 |
| 10 | 7.5 | 450 |
| 11 | 7.5 | 300 |
| 12 | 8 | 160 |
| 13 | 4 | 400 |

Example 9

HPLC Analysis of the chromatographic behavior of insulin/betaine formulations.

Specific Aim:

This experiment is intended to reveal the existence of molecular interactions between bovine insulin and betaine by comparing the chromatographic profiles of these compounds alone to their mixtures.

The HPLC chromatography carried out in the reversed phase mode will allow resolving the putative molecular complexes from the free species based mainly on difference of relative hydrophobicity. This separation will be performed in a binary mixture of water-acetonitrile with trifluoroacetic acid (TFA) 0.1%.

General Procedure.

Bovine Insulin—Sigma—Ref I 5500

Betaine anhydrous pharmaceutical grade

Insulin has been solubilized in acetic acid at pH 2-3.

The insulin/betaine complexes have been prepared according to the standard operation procedure:

Betaine powder has been dissolved directly in the insulin solution according to compositions summarized in table I.

Insulin solution has been injected with an automatic pipette in a requested amount of betaine powder directly weighted in glass tube.

The dissolution of betaine in the insulin solution has been realized by pipetting up and down 3-4 times

TABLE I

Recipe for the preparation of the insulin/betaine mixtures + corresponding controls

| Tube n° | Formulation conditions (betaine/insulin wt ratio) | Weight (mg) of betaine to add to 2 mL insulin solution (0.357 mg/mL) | Insulin (0.357 mg/mL) | Diluent (mL) |
|---|---|---|---|---|
| 1 | Insulin control | | 2 | 0 |
| 2 | Insulin control | | 2 | 0 |
| 3 | Betaine/insulin (14) | 10 | 2 | 0 |
| 4 | Betaine/insulin (28) | 20 | 2 | 0 |
| 5 | Betaine/insulin (56) | 40 | 2 | 0 |
| 6 | Betaine/insulin (140) | 100 | 2 | 0 |
| 7 | Betaine/insulin (280) | 200 | 2 | 0 |
| 8 | Betaine/insulin (420) | 300 | 2 | 0 |
| 9 | Betaine ctrl (14) | 10 | 0 | 2 |
| 10 | Betaine ctrl (28) | 20 | 0 | 2 |
| 11 | Betaine ctrl (56) | 40 | 0 | 2 |
| 12 | Betaine ctrl (140) | 100 | 0 | 2 |
| 13 | Betaine ctrl (280) | 200 | 0 | 2 |
| 14 | Betaine ctrl (420) | 300 | 0 | 2 |
| 15 | Diluent | 0 | 0 | 2 |

After formulation the mixtures have been equilibrated at RT for 30 min. Afterwards they have been filtrated on 0.45 μm polysulfone filter.

0.1 mL of all these 15 formulations have been diluted in Coulter-Beckman HPLC glass vials filled already with:
  either 900 μL of injectable water
  either 900 μL of the starting mobile phase: [32 (V/V) % water (TFA: 0.1 (V/V) %)–68 (V/V) % acetonitrile (TFA: 0.1 (V/V) %]

The HPLC analyses of insulin have been performed adopting the following experimental details:
  column C18: Lichrosphere, 100 Merck
  the establishment of water (TFA 0.11%)—acetonitrile (TFA 0.1%) gradient.
  a UV detection Beckman 266; 210 nm—RT.

Samples have been stored at room temperature until their analysis.

Results

Figure 5:
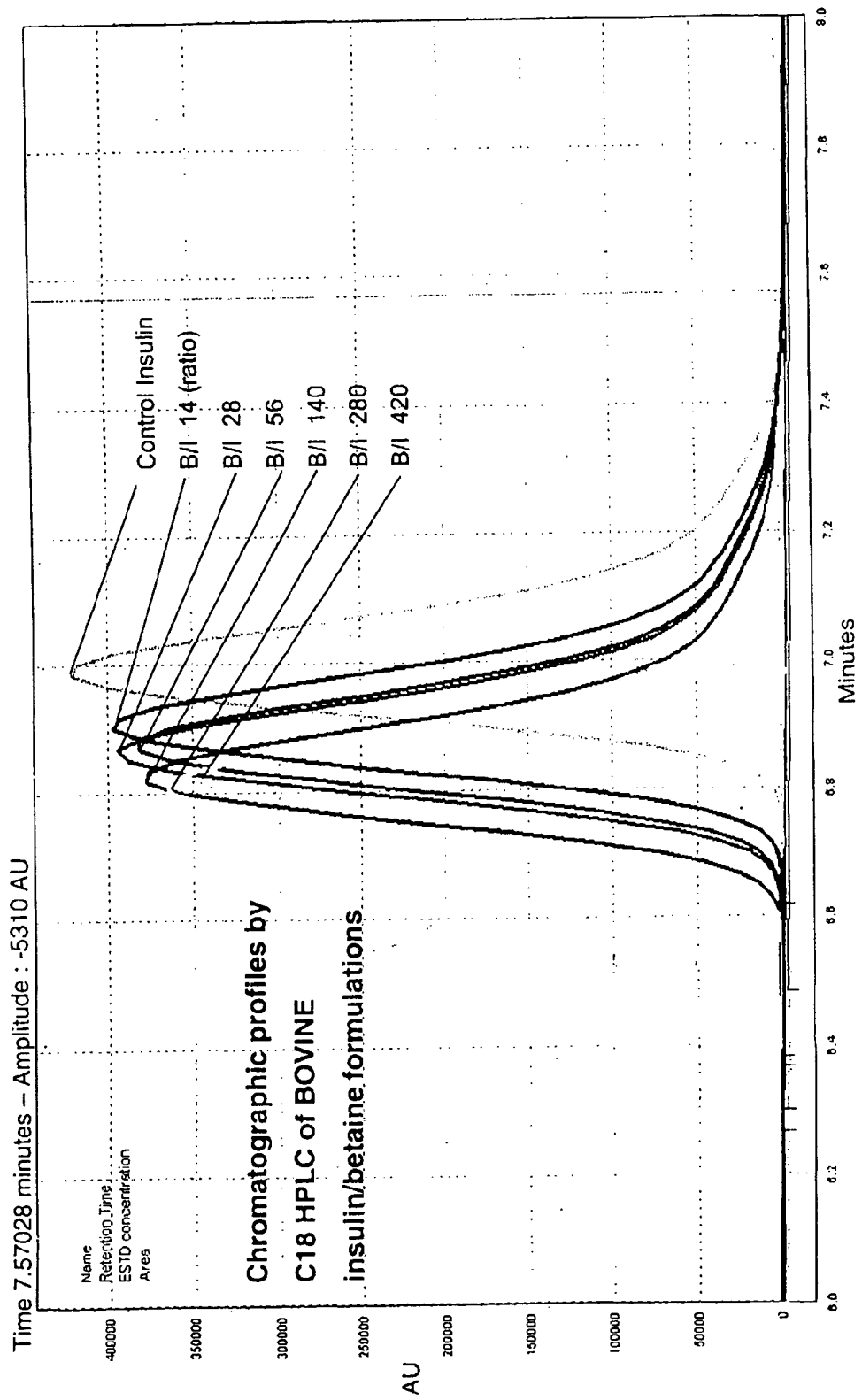
FIG. 5 illustrates the different chromatographic profiles, as determined by high performance liquid chromatography (HPLC), of various betaine/bovine insulin formulations.

All the formulations were transparent, non colored and stable. The HPLC analysis of the different insulin formulations are presented in table II their corresponding chromatograms are provided in FIG. 5.

TABLE II

HPLC data of samples injected in time sequence increasing betaine/human insulin wt ratios. The retention times (mode of the peak) of insulin and corresponding areas at 210 nm are mentioned as well as the % of area of insulin peak versus Insulin control.

| | Betaine/bovine insulin samples diluted in water | | |
|---|---|---|---|
| | RT (min) | Area | Area % of insulin control(*) |
| Insulin control | 7.350 | 4395211 | 100.0 |
| | 7.333 | 4426823 | |
| Betaine/Insulin 14 | 7.333 | 4364703 | 99.0 |
| Betaine/Insulin 28 | 7.317 | 4295962 | 97.4 |
| Betaine/Insulin 56 | 7.350 | 4165125 | 94.4 |
| Betaine/Insulin 140 | 7.317 | 4013583 | 91.0 |
| Betaine/Insulin 280 | 7.300 | 3849583 | 87.3 |
| Betaine/Insulin 420 | 7.267 | 3647269 | 82.7 |

(*) Insulin control: mean of Insulin control diluted in water

Example 10

The experimental scheme of example 9 has been repeated but using human insulin instead of bovine insulin. Insulin Human (expressed in yeast)—Sigma—Ref 12643

Results

Figure 6:
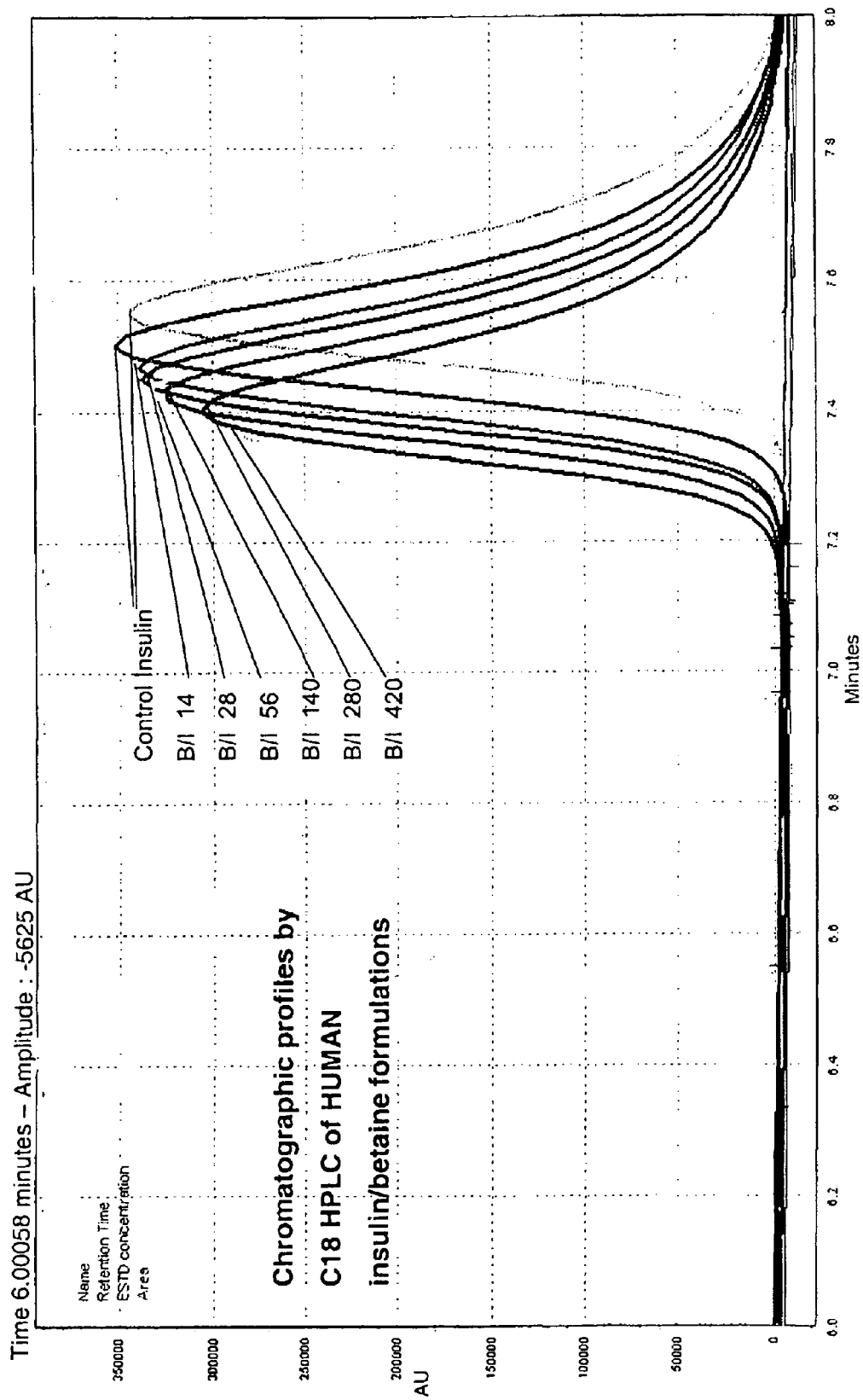
FIG. 6 illustrates the different chromatographic profiles, as determined by HPLC, of various betaine/human insulin formulations.

All the formulations were transparent, non colored and stable. The HPLC analysis of the different insulin formulations are presented in table II their corresponding chromatograms are provided in FIG. 6.

TABLE II

HPLC data of samples injected in time sequence increasing betaine/human insulin wt ratios. The retention times (mode of the peak) of insulin and corresponding areas at 210 nm are mentioned as well as the % of area of insulin peak versus Insulin control.

| | Betaine/human insulin samples diluted in water | | |
|---|---|---|---|
| | RT (min) | Area | Area % of insulin control(*) |
| Insulin control | 7.550 | 5086761 | 100.0 |
| | 7.500 | 5082534 | |
| Betaine/Insulin 14 | 7.467 | 5035891 | 99.0 |
| Betaine/Insulin 28 | 7.450 | 49110529 | 96.6 |

TABLE II-continued

HPLC data of samples injected in time sequence increasing betaine/human insulin wt ratios. The retention times (mode of the peak) of insulin and corresponding areas at 210 nm are mentioned as well as the % of area of insulin peak versus Insulin control.

| | Betaine/human insulin samples diluted in water | | |
|---|---|---|---|
| | RT (min) | Area | Area % of insulin control(*) |
| Betaine/Insulin 56 | 7.433 | 4834182 | 95.1 |
| Betaine/Insulin 140 | 7.433 | 4737122 | 93.2 |
| Betaine/Insulin 280 | 7.400 | 4457865 | 87.7 |
| Betaine/Insulin 420 | 7.383 | 4244116 | 83.5 |

(*) Insulin control: mean of Insulin control diluted in water

Discussion

The HPLC reveals the existence of a decrease of surface of the insulin peak observed when raising the betaine/insulin ratio is consistent, ratio dependent and reproducible whatever the time sequence of sample injection or the insulin used (bovine or human). This decrease of surface of peak (16 to 17% at the highest betaine/insulin ratio) as already noticed with bovine insulin.

This decrease clearly shows that:
  The change of surface properties of insulin when complexed with betaine promotes a partial adsorption of insulin on the C18 support, thereby decreasing its recovery
  A change of molar extinction coefficient of insulin at 210 nm when this polypeptide is combined with betaine.

This ratio dependency of the height of the pick is to be correlated to enhanced and/or modified in vivo characteristics of the insulin/betaine complexes. Depending of the mode of administration, one can modulate the ratios as to obtain the desired profiles.

These tests clearly show the obtaining of new chemical entities when mixing betaine and insulin in selected conditions as in selected ratios.

Such new chemical entities being obtained after a process consisting of one or more step selected from the group consisting of: filtration, drying, freezing, crystallization, mixing, vortexing, trituration, powdering, emulsion, micro/nano emulsion, micro/nano powdering and theirs pharmaceutical acceptable combinations, before possibly being submitted after their obtaining, to one or more process selected from the group consisting of filtration, drying, freezing, crystallization, mixing, vortexing, trituration, powdering, emulsion, micro/nano emulsion, micro/nano powdering and theirs pharmaceutical acceptable combinations.

The invention claimed is:

1. A pharmaceutical combination comprising (a) a therapeutic effective amount of an insulin compound selected from the group consisting of insulin, insulin analogues and mixtures thereof, and (b) a therapeutic effective amount of a pharmaceutically acceptable betaine of general formula $(CH_3)_3N^+—(CH_2)n—COO^-$; with n being an integer from 1 to 5, in which the insulin and the betaine form at least partly a structure selected from the group consisting of chemical entity, chemical complex, physico complex, insulin/betaine micelles, insulin/betaine microstructures, insulin/betaine nanostructures, and combinations thereof, and in which the weight ratio of therapeutic effective amount of the insulin compound/therapeutic effective amount of betaine is between 1:400 and 1:5.

2. The pharmaceutical combination of claim 1, in which the therapeutic effective amount of betaine is selected from the group consisting of therapeutic effective amount of betaine suitable for reducing the onset of action of the insulin compound after administration in a human, therapeutic effective amount of betaine suitable for extending the duration of action of the therapeutic effective amount of insulin compound after administration in a human, and therapeutic effective amount of betaine suitable for reducing the onset of action of the insulin compound and for extending the duration of action of the therapeutic effective amount of insulin compound after administration in a human, and in which the weight ratio of therapeutic effective amount of the insulin compound/therapeutic effective amount of betaine is between 1:100 and 1:5.

3. The pharmaceutical combination of claim 1, in which the therapeutic effective amount of betaine is suitable for increasing the duration of action of the therapeutic effective amount of insulin compound after administration in a human by at least 30% with respect to the duration of action of the same therapeutic effective amount of insulin compound after administration in a human without betaine.

4. The pharmaceutical combination of claim 1, which comprises a therapeutic effective amount of betaine for increasing the efficiency of the therapeutic effective amount of insulin compound at least for a period of 2 to 24 hours after administration in a human of the combination.

5. The pharmaceutical combination of claim 1, in which the in vivo total bioavailability of the therapeutic effective amount of insulin compound after human administration is increased by at least 20% with respect to the in vivo total bioavailability of said therapeutic effective amount of the insulin compound after administration in a human without betaine.

6. The pharmaceutical effective combination of claim 1, which comprises a daily therapeutic effective dose of the insulin compound corresponding to less than 80% of the daily therapeutic effective amount of said insulin compound administered in a human without betaine.

7. The pharmaceutical combination of claim 1, in which the insulin compound and the betaine form a structure selected from the group consisting of a complex in which the insulin compound is at least micro-dispersed in a betaine phase, a complex in which the insulin compound is at least nano-dispersed in a betaine phase, a complex in which the insulin compound is at least partly dissolved in a betaine phase, a complex comprising a core comprising insulin compound and an envelope comprising betaine surrounding at least partly said core, and combinations of said complexes.

8. The pharmaceutical combination of claim 1, in which at least 50% by weight of the insulin compound and the betaine present in the combination form a physico complex selected from the group consisting of co-precipitates of insulin compound and betaine, co-crystals of insulin compound and betaine, and mixtures of said co-precipitates and co-crystals.

9. The pharmaceutical combination of claim 1, in which the insulin compound and the betaine are at least partly entrapped as a mix in capsules selected from the group consisting of microcapsules, nanocapsules, and mixtures thereof.

10. The pharmaceutical combination of claim 1, in which at least 10% by weight of the insulin compound is entrapped in a betaine structure selected from the group consisting of betaine microcapsules, betaine nanocapsules, betaine meso structures, betaine micro structures, betaine nanostructures and mixtures thereof.

11. The pharmaceutical combination of claim 1, in which the insulin compound and the betaine are entrapped at least partly in a structure selected from the group consisting of liposomes, multiple liposomal formulations and combinations thereof.

12. The pharmaceutical combination of claim 1, which comprises beads or particles comprising pharmaceutically acceptable betaine and insulin compound, said beads or particles being provided with a water insoluble entero soluble polymer coating.

13. A pharmaceutical composition combining:
   a form A comprising a pharmaceutically acceptable short-acting insulin compound selected from the group consisting of short-acting insulins and their analogues, said form being free of betaine of general formula $(CH_3)_3N^+-(CH_2)n-COO^-$, and
   a form B comprising a mixture of:
   a. a pharmaceutically acceptable insulin compound selected from the group consisting of short acting insulins, intermediate-acting insulins, long-acting insulins, analogues thereof and their mixtures, and
   b. a pharmaceutically acceptable betaine of general formula $(CH_3)_3N_+-(CH_2)n-COO^-$; with n being an integer from 1 to 5.

14. The pharmaceutical composition of claim 13, in which the form B comprises short-acting insulin dispersed in a betaine containing phase.

15. The pharmaceutical composition of claim 13, which comprises an amount of form A and an amount of form B with a weight ratio of form A/form B of between 0.1 and 1.

16. The pharmaceutical composition of claim 13, which comprises an amount of form A and an amount of form B with a weight ratio of form B/form A of between 0.1 and 1.

17. The pharmaceutical composition of claim 13, in which the form B is separated from the form A by a controlled-release layer.

18. The pharmaceutical composition of claim 13, in which the form B comprises a co-crystal of the insulin compound and the betaine, 19. An isotonic aqueous composition comprising (a) a therapeutic effective amount of an insulin compound selected from the group consisting of insulin, insulin analogues and mixtures thereof, and (b) a therapeutic effective amount of a pharmaceutically acceptable betaine of general formula $(CH_3)_3N^+-(CH_2)n-COO^-$; with n being an integer from 1 to 5, in which the insulin and the betaine form at least partly a structure selected from the group consisting of chemical entity, chemical complex, physic complex, insulin/betaine micelles, insulin/betaine microstructures, insulin/betaine nanostrucures, and combinations thereof, and in which the weight ratio of therapeutic effective amount of the insulin compound/therapeutic effective amount of betaine is between 1:100 and 1:5.

20. The pharmaceutical combination of claim l, wherein said combination is in a dosage form suitable for an administration route selected from the group consisting of oral, dermal, transdermal, subcutaneous, parenteral, intraperitoneal, sublingual, nasal, pulmonary, rectal, and combinations thereof.

* * * * *